US006511845B1

(12) United States Patent
Davis et al.

(10) Patent No.: US 6,511,845 B1
(45) Date of Patent: Jan. 28, 2003

(54) METHODS FOR PRODUCING AN IMMUNE RESPONSE AGAINST HIV-1

(76) Inventors: Alan R. Davis, 4411 Oak Forest Dr., Missouri City, TX (US) 77459; Paul P. Hung, 506 Ramblewood Dr., Bryn Mawr, PA (US) 19010; Michael D. Lubeck, 2265 Spangler Rd., York, PA (US) 17402; Robert J. Natuk, 63 Vones La., Raritan, NJ (US) 08869; Pranab K. Chanda, 30 Zaitz Farm Rd., West Windsor, NJ (US) 08550; Shridhara C. S. Murthy, 4677 Erin Ct., Ann Arbor, MI (US) 48105; Shaw-Guang L. Lee, 155 S. Spring Mill Rd., Villanova, PA (US) 19085

( * ) Notice: Subject to any disclaimer, the term of this patent is extended or adjusted under 35 U.S.C. 154(b) by 13 days.

(21) Appl. No.: 09/618,360

(22) Filed: Jul. 18, 2000

Related U.S. Application Data

(63) Continuation of application No. 09/457,421, filed on Dec. 7, 1999, which is a continuation-in-part of application No. 08/276,289, filed on Jul. 20, 1994, now abandoned, which is a continuation-in-part of application No. 08/105,232, filed on Aug. 11, 1993, now abandoned, which is a continuation-in-part of application No. 07/926,491, filed on Aug. 7, 1992, now abandoned.

(51) Int. Cl.[7] .................. A61K 39/21; A61K 39/235; C12N 15/01; C12N 15/07; C12N 15/48
(52) U.S. Cl. .................. 435/320.1; 424/93.1; 424/96.1; 424/208.1; 424/233.1; 424/199.1; 435/69.1
(58) Field of Search .................. 424/199.1, 208.1, 424/233.1, 93.1, 96.1; 435/320.1, 69.1

(56) References Cited

U.S. PATENT DOCUMENTS 4,920,209 A 4/1990 Davis et al.

FOREIGN PATENT DOCUMENTS

| EP | 80806 | 6/1983 |
|---|---|---|
| GB | 2166349 B | 10/1988 |
| WO | WO83/02393 | 7/1983 |
| WO | WO91/13909 | 9/1991 |

OTHER PUBLICATIONS

Rober–Guroff et al. J. Virol. 1998, vol. 72, pp. 10275–10280.*
Fahey et al. Clin. Exp. Immunol. 1992, vol. 88, pp. 1–5.*
Fox BiolTechnology 1994, vol. 12, pp. 128.*
Haynes et al. Ann. Med/ 1996, vol. 28, pp. 39–41.*
Dombrowski et al. Infection (2000,) vol. 28, pp. 323–325.*
Jon Cohen Science (2001), vol. vol. 292, pp. 24–25*
Natru et al. Dev. Biol. Stamd. 1995, vol. 84, pp. 153–156.*
Vaccine Res. 1:275 (1992).
Virology 175:535 (1990).
J. Gen. Virology 72:1243 (1991).
Cell 46:807 (1986).
Nature 321:412 (1986).
Vaccine 10:475 (1992).
J. Virol. 66:4407 (1992).
Arch, Virol. 100:279 (1988).
J. Infect. Dis. 162:1177 (1990).
Nat. Immun. Cell Growth Regul. 7:135 (1988).
Proc. Natl. Acad. Sci. USA 84:4626 (1987).
Intern. Rev. Immunol. 7:67 (1990).
Cell 41:979 (1985).
Science 234:1392 (1986).
J. Virol. 61:2024 (1987).
Proc. Natl. Acad. Sci. USA 84:3797 (1987).
Bio/Technology 3:905 (1985).
J. Infect. Dis. 157:149 (1988).
Nature 320:535 (1986).
J. Virol. 63:129 (1989).
Proc. Natl. Acad. Sci. USA 85:334 (1988).
J. Virol. 62:4185 (1988).
Vaccine 5:90 (1987).
Nature 328:721 (1978).
Proc. Natl. Acad. Sci. USA 84:6294 (1987).
J. Virol. 61:3617 (1987).
Proc. Natl. Acad. Sci. USA 85:5200 (1988).
J. Immunol. 139:988 (1987).
Proc. Natl. Acad. Sci. USA 85:4478 (1988).
Nature 332:728 (1988).
Proc. Natl. Acad. Sci. USA 82:4813 (1985).
Proc. Natl. Acad. Sci. USA 86:6353 (1989).
Science 220:868 (1983).
Science 224:500 (1984).
Science 224:497 (1984).
Science 224:506 (1984).
J. AIDS 6:681 (1993).
AIDS Res. and Human Retroviruses 9:395 (1993).
Vaccine Res. 1:275 (1992).
Natuk, R., Recombinant Vectors in Vaccine Dev., Brown, ed., vol. 82, 71 (1994).
Natuk, R., Huitieme Colloque Des Cent Gardes 115 (1993).
AIDS Res. and Human Retroviruses 10:1443 (1994).
J. Virol. 71:8531 (1997).
J. Virol. 73:7430 (1999).
Nature Medicine 3:651 (1997).
Biochimica et Biophysica Acta. 989:301 (1989).
Science 260:1279 (1993).

* cited by examiner

Primary Examiner—Ali R. Salimi
Assistant Examiner—Bao Qun Li
(74) Attorney, Agent, or Firm—Bill T. Brazil; Alan M. Gordon

(57) ABSTRACT

This invention provides a method of protecting a primate from an infectious organism by stimulating the production of antibodies or cell mediated immunity to the infectious organism which comprises administering to said primate intranasally, intramuscularly, or subcutaneously, live recombinant adenoviruses in which the virion structural protein is unchanged from that in the native adenovirus from which the recombinant adenovirus is produced, and which contain the gene coding for the antigen corresponding to said antibodies or inducing said cell mediated immunity. Preferably, the infectious organism is HIV and the primate is a human.

24 Claims, 16 Drawing Sheets

```
              10         20         30         40         50
              |          |          |          |          |
     AGACCCTTCC TCCTCTGATC CAGGACTCTA ACTCTACCTT ACCAGCACCA
                                                         ==>
                                                         ==>
                                                         ==>
                                                         ==>
                                                         ==>
                                                         ==>
                                                         ==>

60         70         80         90        100
              |          |          |          |          |
     TCCACTACTA ACCTTCCCGA AACTAACAAG CTTCTAGCAC TGTCTTCCGG
                                           ..  ..........
                                           AC TGTCTTCCGG
                                                         ==>
                                                         ==>
                                                         ==>
                                                         ==>
                                                         ==>
                                                         ==>

110        120        130        140        150
              |          |          |          |          |
     ATCGCTGTCC AGGAGCGCCA GCTGTTGGGC TCGCGGTTGA GAAGGTATTC
     .......... .......... .......... .......... ..........
     ATCGCTGTCC AGGAGCGCCA GCTGTTGGGC TCGCGGTTGA GAAGGTATTC
                                                         ==>
                                                         ==>
                                                         ==>
                                                         ==>
                                                         ==>
                                                         ==>

160        170        180        190        200
              |          |          |          |          |
     TTCGTCATCC TTCCAGTACT CTTCGAGGGG AAACCCGTCT TTTTCTGCAC
     .......... .......... .......... .......... ..........
     TTCGTCATCC TTCCAGTACT CTTCGAGGGG AAACCCGTCT TTTTCTGCAC
                                                         ==>
                                                         ==>
                                                         ==>
                                                         ==>
                                                         ==>
                                                         ==>

210        220        230        240        250
              |          |          |          |          |
     GGTACTCCGC GCAAGGACCT GATTGTCTCA AGATCCACGG GATCTGAAAA
     .......... .......... .......... .......... ..........
     GGTACTCCGC GCAAGGACCT GATTGTCTCA AGATCCACGG GATCTGAAAA
                                                         ==>
                                                         ==>
                                                         ==>
                                                         ==>
                                                         ==>
                                                         ==>
```

FIG.2A

```
              260        270        280        290        300
               |          |          |          |          |
        CCTTTCGACG AAAGCGTCTA ACCAGTCGCA ATCGCAAGAA GCTTGTCGAG
        .......... .......... .......... ..........
        CCTTTCGACG AAAGCGTCTA ACCAGTCGCA ATCGCAAG
                                                        ==>
                                                        ==>
                                                        ==>
                                                        ==>
                                                        ==>
                                                        ==>

310        320        330        340        350
               |          |          |          |          |
        CCACCATGAG AGTGAAGGGG ATCAGGAGGA ATTATCAGCA CTGGTGGGGA
        <==
        <==
        *.*....... .......... .......... .......... ..........
          GCAATGAG AGTGAAGGGG ATCAGGAGGA ATTATCAGCA CTGGTGGGGA
                                                        ==>
                                                        ==>
                                                        ==>
                                                        ==>

360        370        380        390        400
               |          |          |          |          |
        TGGGGCACGA TGCTCCTTGG GTTATTAATG ATCTGTAGTG CTACAGAAAA
        <==
        <==
        .......... .......... .......... .......... ..........
        TGGGGCACGA TGCTCCTTGG GTTATTAATG ATCTGTAGTG CTACAGAAAA
                                                        ==>
                                                        ==>
                                                        ==>
                                                        ==>

410        420        430        440        450
               |          |          |          |          |
        ATTGTGGGTC ACAGTCTATT ATGGGGTACC TGTGTGGAAA GAAGCAACCA
        <==
        <==
        .......... .......... .......... .......... ..........
        ATTGTGGGTC ACAGTCTATT ATGGGGTACC TGTGTGGAAA GAAGCAACCA
                                                        ==>
                                                        ==>
                                                        ==>
                                                        ==>

460        470        480        490        500
               |          |          |          |          |
        CCACTCTATT TTGTGCATCA GATGCTAAAG CATATGATAC AGAGGTACAT
        <==
        <==
        .......... .......... .......... .......... ..........
        CCACTCTATT TTGTGCATCA GATGCTAAAG CATATGATAC AGAGGTACAT
                                                        ==>
                                                        ==>
                                                        ==>
                                                        ==>
```

FIG. 2B

```
              510        520        530        540        550
               |          |          |          |          |
    AATGTTTGGG CCACACATGC CTGTGTACCC ACAGACCCCA ACCCACAAGA
    <==
    <==
    ---------- ---------- ---------- ---------- ----------
    AATGTTTGGG CCACACATGC CTGTGTACCC ACAGACCCCA ACCCACAAGA
                                                        ==>
                                                        ==>
                                                        ==>
                                                        ==>

560        570        580        590        600
               |          |          |          |          |
    AGTAGAATTG GTAAATGTGA CAGAAAATTT TAACATGTGG AAAAATAACA
    <==
    <==
    ---------- ---------- ---------- ---------- ----------
    AGTAGAATTG GTAAATGTGA CAGAAAATTT TAACATGTGG AAAAATAACA
                                                        ==>
                                                        ==>
                                                        ==>
                                                        ==>

610        620        630        640        650
               |          |          |          |          |
    TGGTAGAACA GATGCATGAG GATATAATCA GTTTATGGGA TCAAAGCCTA
    <==
    <==
    ---------- ---------- ---------- ---------- ----------
    TGGTAGAACA GATGCATGAG GATATAATCA GTTTATGGGA TCAAAGCCTA
                                                        ==>
                                                        ==>
                                                        ==>
                                                        ==>

660        670        680        690        700
               |          |          |          |          |
    AAGCCATGTG TAAAATTAAC CCCACTCTGT GTTACTTTAA ATTGCACTGA
    <==
    <==
    ---------- ---------- ---------- ---------- ----------
    AAGCCATGTG TAAAATTAAC CCCACTCTGT GTTACTTTAA ATTGCACTGA
                                                        ==>
                                                        ==>
                                                        ==>
                                                        ==>

710        720        730        740        750
               |          |          |          |          |
    TTTGAGGAAT ACTACTAATA CCAATAATAG TACTGCTAAT AACAATAGTA
    <==
    <==
    ---------- ---------- ---------- ---------- ----------
    TTTGAGGAAT ACTACTAATA CCAATAATAG TACTGCTAAT AACAATAGTA
                                                        ==>
                                                        ==>
                                                        ==>
                                                        ==>
```

FIG.2C

```
              760        770        780        790        800
               |          |          |          |          |
ATAGCGAGGG AACAATAAAG GGAGGAGAAA TGAAAAACTG CTCTTTCAAT
<==
<==
---------- ---------- ---------- ---------- ----------
ATAGCGAGGG AACAATAAAG GGAGGAGAAA TGAAAAACTG CTCTTTCAAT
                                                   ==>
                                                   ==>
                                                   ==>
                                                   ==>

810        820        830        840        850
               |          |          |          |          |
ATCACCACAA GCATAAGAGA TAAGATGCAG AAAGAATATG CACTTCTTTA
<==
<==
---------- ---------- ---------- ---------- ----------
ATCACCACAA GCATAAGAGA TAAGATGCAG AAAGAATATG CACTTCTTTA
                                                   ==>
                                                   ==>
                                                   ==>
                                                   ==>

860        870        880        890        900
               |          |          |          |          |
TAAACTTGAT ATAGTATCAA TAAATAATGA TAGTACCAGC TATAGGTTGA
<==
<==
---------- ---------- ---------- ---------- ----------
TAAACTTGAT ATAGTATCAA TAAATAATGA TAGTACCAGC TATAGGTTGA
                                                   ==>
                                                   ==>
                                                   ==>
                                                   ==>

910        920        930        940        950
               |          |          |          |          |
TAAGTTGTAA TACCTCAGTC ATTACACAAG CTTGTCCAAA GATATCCTTT
<==
<==
---------- ---------- ---------- ---------- ----------
TAAGTTGTAA TACCTCAGTC ATTACACAAG CTTGTCCAAA GATATCCTTT
                                                   ==>
                                                   ==>
                                                   ==>
                                                   ==>

960        970        980        990        1000
               |          |          |          |          |
GAGCCAATTC CCATACACTA TTGTGCCCCG GCTGGTTTTG CGATTCTAAA
<==
<==
---------- ---------- ---------- ---------- ----------
GAGCCAATTC CCATACACTA TTGTGCCCCG GCTGGTTTTG CGATTCTAAA
                                                   ==>
                                                   ==>
                                                   ==>
                                                   ==>
```

FIG. 2D

```
          1010       1020       1030       1040       1050
            |          |          |          |          |
GTGTAACGAT AAAAAGTTCA GTGGAAAAGG ATCATGTAAA AATGTCAGCA
<==
<==
.......... .......... .......... .......... ..........
GTGTAACGAT AAAAAGTTCA GTGGAAAAGG ATCATGTAAA AATGTCAGCA
                                                    ==>
                                                    ==>
                                                    ==>
                                                    ==>

1060       1070       1080       1090       1100
            |          |          |          |          |
CAGTACAATG TACACATGGA ATTAGGCCAG TAGTATCAAC TCAACTGCTG
<==
<==
.......... .......... .......... .......... ..........
CAGTACAATG TACACATGGA ATTAGGCCAG TAGTATCAAC TCAACTGCTG
                                                    ==>
                                                    ==>
                                                    ==>
                                                    ==>

1110       1120       1130       1140       1150
            |          |          |          |          |
TTAAATGGCA GTCTAGCAGA AGAAGAGGTA GTAATTAGAT CTGAGAATTT
<==
<==
.......... .......... .......... .......... ..........
TTAAATGGCA GTCTAGCAGA AGAAGAGGTA GTAATTAGAT CTGAGAATTT
                                                    ==>
                                                    ==>
                                                    ==>
                                                    ==>

1160       1170       1180       1190       1200
            |          |          |          |          |
CAATGATAAT GCTAAAACCA TCATAGTACA TCTGAATGAA TCTGTACAAA
<==
<==
.......... .......... .......... .......... ..........
CAATGATAAT GCTAAAACCA TCATAGTACA TCTGAATGAA TCTGTACAAA
                                                    ==>
                                                    ==>
                                                    ==>
                                                    ==>

1210       1220       1230       1240       1250
            |          |          |          |          |
TTAATTGTAC AAGACCCAAC TACAATAAAA CAAAAACCAT ACATATAGGA
<==
<==
.......... .......... .......... .......... ..........
TTAATTGTAC AAGACCCAAC TACAATAAAA CAAAAACCAT ACATATAGGA
                                                    ==>
                                                    ==>
                                                    ==>
                                                    ==>
```

FIG. 2E

```
            1260       1270       1280       1290       1300
              |          |          |          |          |
     CCAGGGAGAG CATTTTATAC AACAAAAAAT ATAATAGGAA CTATAAGACA
     <==
     <==
     ........... .......... .......... .......... ..........
     CCAGGGAGAG CATTTTATAC AACAAAAAAT ATAATAGGAA CTATAAGACA
                                                         ==>
                                                         ==>
                                                         ==>
                                                         ==>

1310       1320       1330       1340       1350
              |          |          |          |          |
     AGCACATTGT AACATTAGTA GAGCAAAATG GAATGACACT TTAAGACAGA
     <==
     <==
     ........... .......... .......... .......... ..........
     AGCACATTGT AACATTAGTA GAGCAAAATG GAATGACACT TTAAGACAGA
                                                         ==>
                                                         ==>
                                                         ==>
                                                         ==>

1360       1370       1380       1390       1400
              |          |          |          |          |
     TAGTTAGCAA ATTAAAAGAA CAATTTAAGA ATAAAACAAT AGTCTTTAAT
     <==
     <==
     ........... .......... .......... .......... ..........
     TAGTTAGCAA ATTAAAAGAA CAATTTAAGA ATAAAACAAT AGTCTTTAAT
                                                         ==>
                                                         ==>
                                                         ==>
                                                         ==>

1410       1420       1430       1440       1450
              |          |          |          |          |
     CAATCCTCAG GAGGGGACCC AGAAATTGTA ATGCACAGTT TTAATTGTGG
     <==
     <==
     ........... .......... .......... .......... ..........
     CAATCCTCAG GAGGGGACCC AGAAATTGTA ATGCACAGTT TTAATTGTGG
                                                         ==>
                                                         ==>
                                                         ==>
                                                         ==>

1460       1470       1480       1490       1500
              |          |          |          |          |
     AGGGGAATTT TTCTACTGTA ATACATCACC ACTGTTTAAT AGTACTTGGA
     <==
     <==
     ........... .......... .......... .......... ..........
     AGGGGAATTT TTCTACTGTA ATACATCACC ACTGTTTAAT AGTACTTGGA
                                                         ==>
                                                         ==>
                                                         ==>
                                                         ==>
```

FIG.2F

```
          1510       1520       1530       1540       1550
           |          |          |          |          |
ATGGTAATAA TACTTGGAAT AATACTACAG GGTCAAATAA CAATATCACA
<==
<==
.......... .......... .......... .......... ..........
ATGGTAATAA TACTTGGAAT AATACTACAG GGTCAAATAA CAATATCACA
                                                   ==>
                                                   ==>
                                                   ==>
                                                   ==>

1560       1570       1580       1590       1600
           |          |          |          |          |
CTTCAATGCA AAATAAAACA AATTATAAAC ATGTGGCAGG AAGTAGGAAA
<==
<==
.......... .......... .......... .......... ..........
CTTCAATGCA AAATAAAACA AATTATAAAC ATGTGGCAGG AAGTAGGAAA
                                                   ==>
                                                   ==>
                                                   ==>
                                                   ==>

1610       1620       1630       1640       1650
           |          |          |          |          |
AGCAATATAT GCCCCTCCCA TTGAAGGACA AATTAGATGT TCATCAAATA
<==
<==
.......... .......... .......... .......... ..........
AGCAATATAT GCCCCTCCCA TTGAAGGACA AATTAGATGT TCATCAAATA
                                                   ==>
                                                   ==>
                                                   ==>
                                                   ==>

1660       1670       1680       1690       1700
           |          |          |          |          |
TTACAGGGCT ACTATTAACA AGAGATGGTG GTAAGGACAC GGACACGAAC
<==
<==
.......... .......... .......... .......... ..........
TTACAGGGCT ACTATTAACA AGAGATGGTG GTAAGGACAC GGACACGAAC
                                                   ==>
                                                   ==>
                                                   ==>
                                                   ==>

1710       1720       1730       1740       1750
           |          |          |          |          |
GACACCGAGA TCTTCAGACC TGGAGGAGGA GATATGAGGG ACAATTGGAG
<==
.......... .......... .......... .......... ..........
GACACCGAGA TCTTCAGACC TGGAGGAGGA GATATGAGGG ACAATTGGAG
                                                   ==>
                                                   ==>
                                                   ==>
                                                   ==>
```

FIG.2G

```
            1760       1770       1780       1790       1800
             |          |          |          |          |
  AAGTGAATTA TATAAATATA AAGTAGTAAC AATTGAACCA TTAGGAGTAG
  <==
  <==
  ---------- ---------- ---------- ---------- ----------
  AAGTGAATTA TATAAATATA AAGTAGTAAC AATTGAACCA TTAGGAGTAG
                                                      ==>
                                                      ==>
                                                      ==>

1810       1820       1830       1840       1850
             |          |          |          |          |
  CACCCACCAA GGCAAAGAGA AGAGTGGTGC AGAGAGAAAA AAGAGCAGCG
  <==
  <==
  ---------- ---------- ---------- ---------- ----------
  CACCCACCAA GGCAAAGAGA AGAGTGGTGC AGAGAGAAAA AAGAGCAGCG
                                                      ==>
                                                      ==>
                                                      ==>
                                                      ==>

1860       1870       1880       1890       1900
             |          |          |          |          |
  ATAGGAGCTC TGTTCCTTGG GTTCTTAGGA GCAGCAGGAA GCACTATGGG
  <==
  <==
  ---------- ---------- ---------- ---------- ----------
  ATAGGAGCTC TGTTCCTTGG GTTCTTAGGA GCAGCAGGAA GCACTATGGG
                                                      ==>
                                                      ==>
                                                      ==>
                                                      ==>

1910       1920       1930       1940       1950
             |          |          |          |          |
  CGCAGCGTCA GTGACGCTGA CGGTACAGGC CAGACTATTA TTGTCTGGTA
  <==
  <==
  ---------- ---------- ---------- ---------- ----------
  CGCAGCGTCA GTGACGCTGA CGGTACAGGC CAGACTATTA TTGTCTGGTA
                                                      ==>
                                                      ==>
                                                      ==>
                                                      ==>

1960       1970       1980       1990       2000
             |          |          |          |          |
  TAGTGCAACA GCAGAACAAT TTGCTGAGGG CCATTGAGGC GCAACAGCAT
  <==
  <==
  ---------- ---------- ---------- ---------- ----------
  TAGTGCAACA GCAGAACAAT TTGCTGAGGG CCATTGAGGC GCAACAGCAT
                                                      ==>
                                                      ==>
                                                      ==>
                                                      ==>
```

FIG.2H

```
              2010       2020       2030       2040       2050
               |          |          |          |          |
ATGTTGCAAC TCACAGTCTG GGGCATCAAG CAGCTCCAGG CAAGAATCCT
<==
<==
.......... .......... .......... .......... ..........
ATGTTGCAAC TCACAGTCTG GGGCATCAAG CAGCTCCAGG CAAGAATCCT
                                                     ==>
                                                     ==>
                                                     ==>
                                                     ==>

2060       2070       2080       2090       2100
               |          |          |          |          |
GGCTGTGGAA AGATACCTAA AGGATCAACA GCTCCTGGGG ATTTGGGGTT
<==
<==
.......... .......... .......... .......... ..........
GGCTGTGGAA AGATACCTAA AGGATCAACA GCTCCTGGGG ATTTGGGGTT
                                                     ==>
                                                     ==>
                                                     ==>
                                                     ==>

2110       2120       2130       2140       2150
               |          |          |          |          |
GCTCTGGAAA ACTCATTTGC ACCACTACTG TGCCTTGGAA TGCTAGTTGG
<==
<==
.......... .......... .......... .......... ..........
GCTCTGGAAA ACTCATTTGC ACCACTACTG TGCCTTGGAA TGCTAGTTGG
                                                     ==>
                                                     ==>
                                                     ==>
                                                     ==>

2160       2170       2180       2190       2200
               |          |          |          |          |
AGTAATAAAT CTCTGGATGA TATTTGGAAT AACATGACCT GGATGCAGTG
<==
<==
.......... .......... .......... .......... ..........
AGTAATAAAT CTCTGGATGA TATTTGGAAT AACATGACCT GGATGCAGTG
                                                     ==>
                                                     ==>
                                                     ==>
                                                     ==>

2210       2220       2230       2240       2250
               |          |          |          |          |
GGAAAGAGAA ATTGACAATT ACACAAGCTT AATATACTCA TTACTAGAAA
<==
<==
.......... .......... .......... .......... ..........
GGAAAGAGAA ATTGACAATT ACACAAGCTT AATATACTCA TTACTAGAAA
                                                     ==>
                                                     ==>
                                                     ==>
                                                     ==>
```

FIG. 21

```
                2260       2270       2280       2290       2300
                  |          |          |          |          |
        AATCGCAAAC CCAACAAGAA ATGAATGAAC AAGAATTATT GGAATTGGAT
        <==
        <==
        .......... .......... .......... .......... ..........
        AATCGCAAAC CCAACAAGAA ATGAATGAAC AAGAATTATT GGAATTGGAT
                                                            ==>
                                                            ==>
                                                            ==>
                                                            ==>

2310       2320       2330       2340       2350
                  |          |          |          |          |
        AAATGGGCAA GTTTGTGGAA TTGGTTTGAC ATAACAAATT GGCTGTGGTA
        <==
        <==
        .......... .......... .......... .......... ..........
        AAATGGGCAA GTTTGTGGAA TTGGTTTGAC ATAACAAATT GGCTGTGGTA
                                                            ==>
                                                            ==>
                                                            ==>
                                                            ==>

2360       2370       2380       2390       2400
                  |          |          |          |          |
        TATAAAAATA TTCATAATGA TAGTAGGAGG CTTGGTAGGT TTAAGAATAG
        <==
        <==
        .......... .......... .......... .......... ..........
        TATAAAAATA TTCATAATGA TAGTAGGAGG CTTGGTAGGT TTAAGAATAG
                                                            ==>
                                                            ==>
                                                            ==>
                                                            ==>

2410       2420       2430       2440       2450
                  |          |          |          |          |
        TTTTTGCTGT ACTTTCTATA GTGAATAGAG TTAGGCAGGG ATACTCACCA
        <==
        <==
        .......... .......... .......... .......... ..........
        TTTTTGCTGT ACTTTCTATA GTGAATAGAG TTAGGCAGGG ATACTCACCA
                                                            ==>
                                                            ==>
                                                            ==>
                                                            ==>

2460       2470       2480       2490       2500
                  |          |          |          |          |
        TTGTCGTTGC AGACCCGCCC CCCAGTTCCG AGGGGACCCG ACAGGCCCGA
        <==
        <==
        .......... .......... .......... .......... ..........
        TTGTCGTTGC AGACCCGCCC CCCAGTTCCG AGGGGACCCG ACAGGCCCGA
                                                            ==>
                                                            ==>
                                                            ==>
                                                            ==>
```

FIG. 2J

```
              2510       2520       2530       2540       2550
                |          |          |          |          |
AGGAATCGAA GAAGAAGGTG GAGAGAGAGA CAGAGACACA TCCGGTCGAT
<==
<==

..........  ..........  ..........  ..........  ..........
AGGAATCGAA GAAGAAGGTG GAGAGAGAGA CAGAGACACA TCCGGTCGAT
                                                       ==>
                                                       ==>
                                                       ==>
                                                       ==>

2560       2570       2580       2590       2600
                |          |          |          |          |
TAGTGCATGG ATTCTTAGCA ATTATCTGGG TCGACCTGCG GAGCCTGTTC
<==
<==

..........  ..........  ..........  ..........  ..........
TAGTGCATGG ATTCTTAGCA ATTATCTGGG TCGACCTGCG GAGCCTGTTC
                                                       ==>
                                                       ==>
                                                       ==>
                                                       ==>

2610       2620       2630       2640       2650
                |          |          |          |          |
CTCTTCAGCT ACCACCACTT GAGAGACTTA CTCTTGATTG CAGCGAGGAT
<==
<==

..........  ..........  ..........  ..........  ..........
CTCTTCAGCT ACCACCACTT GAGAGACTTA CTCTTGATTG CAGCGAGGAT
                                                       ==>
                                                       ==>
                                                       ==>
                                                       ==>

2660       2670       2680       2690       2700
                |          |          |          |          |
TGTGGAACTT CTGGGACGCA GGGGGTGGGA AGTCCTCAAA TATTGGTGGA
<==
<==

..........  ..........  ..........  ..........  ..........
TGTGGAACTT CTGGGACGCA GGGGGTGGGA AGTCCTCAAA TATTGGTGGA
                                                       ==>
                                                       ==>
                                                       ==>
                                                       ==>

2710       2720       2730       2740       2750
                |          |          |          |          |
ATCTCCTACA GTATTGGAGT CAGGAACTAA AGAGTAGTGC TGTTAGCTTG
<==
<==

..........  ..........  ..........  ..........  ..........
ATCTCCTACA GTATTGGAGT CAGGAACTAA AGAGTAGTGC TGTTAGCTTG
                                                       ==>
                                                       ==>
                                                       ==>
                                                       ==>
```

FIG.2K

```
              2760       2770       2780       2790       2800
               |          |          |          |          |
     CTTAATGCCA CAGATATAGC AGTAGCTGAG GGGACAGATA GGGTTATAGA
     <==
     <==
     .......... .......... .......... .......... ..........
     CTTAATGCCA CAGATATAGC AGTAGCTGAG GGGACAGATA GGGTTATAGA
                                                        ==>
                                                        ==>
                                                        ==>

2810       2820       2830       2840       2850
               |          |          |          |          |
     AGTACTGCAA AGAGCTGGTA GAGCTATTCT CCACATACCT ACAAGAATAA
     <==
     <==
     .......... .......... .......... .......... ..........
     AGTACTGCAA AGAGCTGGTA GAGCTATTCT CCACATACCT ACAAGAATAA
                                                        ==>
                                                        ==>
                                                        ==>
                                                        ==>

2860       2870       2880       2890       2900
               |          |          |          |          |
     GACAGGGCTT GGAAAGGGCT TTGCTATAAT CTAGCACTGT CTTCCGGATC
     <==
     <==
     .......... .......... ........* *.
     GACAGGGCTT GGAAAGGGCT TTGCTATAAG AT
                                          ..... ..........
                                          ACTGT CTTCCGGATC
                                                        ==>
                                                        ==>

2910       2920       2930       2940       2950
               |          |          |          |          |
     GCTGTCCAGG AGCGCCAGCT GTTGGGCTCG CGGTTGAGAA GGTATTCTTC
     <==
     <==
     <==
     <==
     .......... .......... .......... .......... ..........
     GCTGTCCAGG AGCGCCAGCT GTTGGGCTCG CGGTTGAGAA GGTATTCTTC
                                                        ==>
                                                        ==>

2960       2970       2980       2990       3000
               |          |          |          |          |
     GTGATCCTTC CAGTACTCTT CGAGGGGAAA CCCGTCTTTT TCTGCACGGT
     <==
     <==
     <==
     <==
     .......... .......... .......... .......... ..........
     GTGATCCTTC CAGTACTCTT CGAGGGGAAA CCCGTCTTTT TCTGCACGGT
                                                        ==>
                                                        ==>
```

FIG.2L

```
             3010       3020       3030       3040       3050
              |          |          |          |          |
ACTCCGCGCA AGGACCTGAT TGTCTCAAGA TCCACGGGAT CTGAAAACCT
<==
<==
<==
<==
.......... .......... .......... .......... ..........
ACTCCGCGCA AGGACCTGAT TGTCTCAAGA TCCACGGGAT CTGAAAACCT
                                                   ==>
                                                   ==>

3060       3070       3080       3090       3100
              |          |          |          |          |
TTCGACGAAA GCGTCTAACC AGTCGCAATC GCAAGAAGCT TGTCGACTAT
<==
<==
<==
<==
.......... .......... .......... .....
TTCGACGAAA GCGTCTAACC AGTCGCAATC GCAAG
                                           GTCGACTAT
                                           .........

3110       3120       3130       3140       3150
              |          |          |          |          |
GGCAGGAAGA AGCGGAGACA GCGACGAAGA CCTCCTCAAG GCAGTCAGAC
<==
<==
<==
<==
<==
<==
GGCAGGAAGA AGCGGAGACA GCGACGAAGA CCTCCTCAAG GCAGTCAGAC
.......... .......... .......... .......... ..........

3160       3170       3180       3190       3200
              |          |          |          |          |
TCATCAAGTT TCTCTATCAA AGCAACCCCC CACCTAACCC TGAAGGCACA
<==
<==
<==
<==
<==
<==
TCATCAAGTT TCTCTATCAA AGCAACCCCC CACCTAACCC TGAAGGCACA
.......... .......... .......... .......... ..........

3210       3220       3230       3240       3250
              |          |          |          |          |
AGGCAAGCTA GGCGGAACAG GAGGAGGCGG TGGAGGGAAA GGCAAAGGCA
<==
<==
<==
<==
<==
<==
AGGCAAGCTA GGCGGAACAG GAGGAGGCGG TGGAGGGAAA GGCAAAGGCA
.......... .......... .......... .......... ..........
```

FIG.2M

```
              3260       3270       3280       3290       3300
               |          |          |          |          |
   AATTCACTCC ATCTCCGAGA GGATTCTGTC CACCTACCTC GGCAGGTCCG
   <=
   <=
   <=
   <=
   <=
   <=
   AATTCACTCC ATCTCCGAGA GGATTCTGTC CACCTACCTC GGCAGGTCCG
   ---------- ---------- ---------- ---------- ----------
              3310       3320       3330       3340       3350
               |          |          |          |          |
   CGGAACCCGT CCCCCTGCAA CTGCCCCCCC TGGAAAGACT GACCCTGGAC
   <=
   <=
   <=
   <=
   <=
   <=
   CGGAACCCGT CCCCCTGCAA CTGCCCCCCC TGGAAAGACT GACCCTGGAC
   ---------- ---------- ---------- ---------- ----------
              3360       3370       3380       3390       3400
               |          |          |          |          |
   TGCAATGAAG ACTGCGGCAC CTCCGGAACC CAAGGAGTCG GCTCCCCCCA
   <=
   <=
   <=
   <=
   <=
   <=
   TGCAATGAAG ACTGCGGCAC CTCCGGAACC CAAGGAGTCG GCTCCCCCCA
   ---------- ---------- ---------- ---------- ----------
              3410       3420       3430       3440       3450
               |          |          |          |          |
   GATCCTGGTC GAGTCCCCCA CCGTGCTGGA ATCCGGACAA AAGGAGTAGT
   <=
   <=
   <=
   <=
   <=
   <=
   GATCCTGGTC GAGTCCCCCA CCGTGCTGGA ATCCGGACAA AAGGAGTAGT
   ---------- ---------- ---------- ---------- ----------
              3460       3470       3480       3490       3500
               |          |          |          |          |
   CGACTCTAGA AGGTGCACCT ACACCCTGCT AAAGACCCTA TGCGGCCTAA
   <=
   <=
   <=
   <=
   <=
   <=
   CG
   --
```

FIG.2N

```
        3510       3520       3530       3540       3550
         |          |          |          |          |
GAGACCTGCT ACCCATGAAT TAAAAATTAA TAAAAAATCA CTTACTTGAA
<==
<==
<==
<==
<==
<==
<==
<==

3560       3570       3580       3590       3600
         |          |          |          |          |
ATCAGCAATA AGGTCTCTGT TTGGAAAT
<==
<==
<==
<==
<==
<==
<==
<==
```

FIG. 2O

SEQUENCE LISTING

<160> NUMBER OF SEQ ID NOS: 1

<210> SEQ ID NO 1
<211> LENGTH: 3655
<212> TYPE: DNA
<213> ORGANISM: Adenovirus

<400> SEQUENCE: 1

```
agacccttcc tcctctgatc caggactcta actctacctt accagcacca tccactacta      60
accttcccga aactaacaag cttctagcac tgtcttccgg atcgctctcc aggagcgcca     120
gctgttgggc tcgcggttga aaggtattc ttcgtgatcc ttccagtact cttcgagggg      180
aaacccgtct ttttctgcac ggtactccgc gcaaggacct gattgtctca agatccacgg    240
gatctgaaaa cctttcgacg aaagcgtcta accagtcgca atcgcaagaa gcttgtcgag    300
ccaccatgag agtgaagggg atcaggagga attatcagca ctggtgggga tggggcacga   360
tgctccttgg gttattaatg atctgtagtg ctacagaaaa attgtgggtc acagtctatt    420
atggggtacc tgtgtggaaa gaagcaacca ccactctatt ttgtgcatca gatgctaaag    480
catatgatac agaggtacat aatgtttggg ccacacaagc ctgtgtaccc acagacccca    540
acccacaaga gtagaattg gtaaatgtga cagaaaattt taacatgtgg aaaaataaca     600
tggtagaaca gatgcatgag gatataatca gtttatggga tcaaagccta aagccataac    660
cccactctgt gttactttaa attgcactga tttgaggaat actactaata ccaataatag    720
tactgctaat aacaatagta atagcgaggg aacaataaag ggaggagaaa tgaaaaactg   780
ctctttcaat atcaccacaa gcataagaga taagatgcag aaagaatatg cacttcttta    840
taaacttgat atagtatcaa tagataatga tagtaccagc tataggttga taagttgtaa    900
tacctcagtc attacacaag cttgtccaaa gatatccttt gagccaattc ccatacacta    960
ttgtgccccg gctggttttg cgattctaaa atgtaacgat aaaaagttca gtggaaaagg   1020
atcatgtaaa aatgtcagca cagtacaatg tacacatgga attaggcaac tcaactgctg   1080
ttaaatggca gtctagcaga agaagaggta gtaattagat ctgagaattt cactgataat   1140
gctaaaacca tcatagtaca tctgaatgaa tctgtacaaa ttaattgtac aagacccaac   1200
tacaataaaa gaaaaaggat acatatagga ccagggagag cattttatac aacaaaaaat   1260
ataataggaa ctataagaca agcacattgt aacattagta gagcaaaatg gaatgacact   1320
ttaagacaga tagttagcaa attaaaagaa caatttaaga ataaaacaat agtctttaat   1380
caatcctcag gaggggaccc agaaattgta atgcacagtt ttaattgtgg aggggaatttt   1440 ttctactgta atacatcacc actgtttaat agtacttgga atggtaataa tacttggaat   1500
aatactacag ggtcaaataa caatatcaca cttcaatgca aaataaaaca aattataaac   1560
atgtggcagg aagtaggaaa agcaatgtat gcccctccca ttgaaggaca aattagatgt   1620
tcatcaaata ttacagggct actattaaca agagatggtg gtaaggacac ggacacgaac   1680
gacaccgaga tcttcagacc tggaggagga gatatgaggg acaattggag aagtgaatta   1740
tataaatata agtagtaac aattgaacca ttaggagtag cacccaccaa ggcaaagaga    1800
agagtggtgc agagagaaaa aagagcagcg ataggagctc tgttccttgg gttcttagga   1860
gcagcaggaa gcactatggg cgcagcgtca gtgacgctga cggtacaggc cagactatta   1920
ttgtctggta tagtgcaaca gcagaacaat ttgctgaggg ccattgaggc gcaacagcat   1980
atgttgcaac tcacagtctg gggcatcaag cagctccagg caagagtcct ggctgtggaa   2040
```

-continued

```
agatacctaa aggatcaaca gctcctgggg ttttggggtt gctctggaaa actcatttgc    2100
accactactg tgccttggaa tgctagttgg agtaataaat ctctggatga tatttggaat    2160
aacatgacct ggatgcagtg ggaaagagaa attgacaatt acacaagctt aatatactca    2220
ttactagaaa aatcgcaaac ccaacaagaa aagaatgaac aagaattatt ggaattggat    2280
aaatgggcaa gtttgtggaa ttggtttgac ataacaaatt ggctgtggta tataaaaata    2340
ttcataatga tagtaggagg cttggtaggt ttaagaatag tttttgctgt actttctata    2400
gtgaatagag ttaggcaggg atactcacca ttgtcgttgc agacccgccc cccagttccg    2460
aggggacccg acaggcccga aggaatcgaa gaagaaggtg gagagagaga cagagacaca    2520
tccggtcgat tagtgcatgg attcttagca attatctggg tcgacctgcg gagcctgttc    2580
ctcttcagct accaccacag agacttactc ttgattgcag cgaggattgt ggaacttctg    2640
ggacgcaggg ggtgggaagt cctcaaatat tggtggaatc tcctacagta ttggagtcag    2700
gaactaaaga gtagtgctgt tagcttgctt aatgccacag ctatagcagt agctgagggg    2760
acagataggg ttatagaagt actgcaaaga gctggtagag ctattctcca catacctaca    2820
agaataagac agggcttgga aagggctttg ctataatcta gcactgtctt ccggatcgct    2880
gtccaggagc gccagctgtt gggctcgcgg ttgagaaggt attcttcgct gtccaggagc    2940
gccagctgtt gggctcgcgg ttgagaaggt attcttcgtg atccttccag tactcttcga    3000
ggggaaaccc gtctttttct gcacggtgtg atccttccag tactcttcga ggggaaaccc    3060
gtctttttct gcacggtact ccgcgcaagg acctgattgt ctcaagatcc acgggatctg    3120
aaaacctttc gacgaaagcg tctaaccagt cgcaatcgca agaagcttgt cgactatggc    3180
aggaagaagc ggagacagcg acgaagacct cctcaaggca gtcagactca tcaagtttct    3240
ctatcaaagc aacccccccac ctaaccctga aggcacaagg caagctaggc ggaacaggag    3300
gaggcggtgg agggaaaggc aaaggcaaat tcactccatc tccgagagga ttctgtccac    3360
ctacctcggc aggtccgcgg aacccgtccc cctgcaactg cccccctgg aaagactgac    3420 cctggactgc aatgaagact gcggcacctc cggaacccaa ggagtcggct cccccagat    3480 cctggtcgag tcccccaccg tgctggaatc cggcaccaag gagtagtcga ctctagaagg    3540
tgcacctaca ccctgctaaa gacctatgc ggcctaagag acctgctacc catgaattaa    3600
aaattaataa aaaatcactt acttgaaatc agcaataagg tctctgtttg gaaat         3655
```

METHODS FOR PRODUCING AN IMMUNE RESPONSE AGAINST HIV-1

CROSS REFERENCE TO RELATED APPLICATION

This is a continuation of application of Ser. No. 09/457,421, filed on Dec. 7, 1999, which is a continuation-in-part of Ser. No. 08/276,289, filed on Jul. 20, 1994, now abandoned, which is a continuation-in-part of Ser. No. 08/105,232, filed on Aug. 11, 1993, now abandoned, which is a continuation-in-part of Ser. No. 07/926,491, filed on Aug. 7, 1992, now abandoned.

BACKGROUND OF THE INVENTION

A major goal of biomedical research is to provide protection against viral disease through immunization. One approach has been to use killed vaccines. However, large quantities of material are required for killed vaccine in order to retain sufficient antigenic mass. In addition, killed vaccines are often contaminated with undesirable products during their preparation. Heterologous live vaccines, using appropriately engineered adenovirus, which is itself a vaccine, seems like an excellent immunogen [Chanock R., JAMA, 195, 151 (1967)]. Our invention concerns vaccines using adenovirus as a vector.

Presently marketed adenovaccine comprises live, infectious adenoviruses in an enteric-coated dosage form. Upon administration to the patient to be vaccinated, the virus is carried past the upper-respiratory system (where disease-producing infection is thought to occur), and is released in the intestine. In the intestine, the virus reproduces in the gut wall, where, although it is not capable of causing adenoviral disease, nevertheless induces the formation of adenovirus antibodies, thus conferring immunity to adenoviral disease. In our invention, live, infectious adenovirus which has been engineered to contain genes coding for antigens produced by other disease-causing organisms. Upon release the virus will reproduce and separately express both the adenoviral antigen and the pathogen antigen, thereby inducing the formation of antibodies or induce cell mediated immunity to both adenovirus and the other disease-causing organism. By "live virus" is meant, in contradistinction to "killed" virus, a virus which is, either by itself or in conjunction with additional genetic material, capable of producing identical progeny. By "infectious" is meant having the capability to deliver the viral genome into cells.

Roy, in European Patent Publication 80,806 (1983), proposed a method for producing immunity to microbial diseases by the administration of a microbe containing a foreign gene which will express an antigen of a second microbe to which immunity is conferred. He states that preferred oral preparations are enteric coated. Dubelcco proposed recombinant adenovirus vaccines in which the surface protein of adenovirus is modified to contain in its structure a segment of foreign protein which will produce a desired biological response on administration to animals. [PCT International Publication WO 83/02393 (1983)]. Davis discloses oral vaccines derived from recombinant adenoviruses. [UK Patent GB 2166349 B].

Human immunodeficiency virus type 1 (HIV-1) has been etiologically associated with acquired immunodeficiency syndrome (AIDS) and related disorders. [Barre-Sinoussi, F., Science 220: 868 (1983); Gallo, R., Science 224: 500 (1984); Popovic, M., Science 224: 497 (1984); Sarngadharan, M., Science 224: 506 (1984)]. AIDS is now a worldwide epidemic for which, currently, there is no vaccine or cure. Most of the effort for vaccine development has focused on the envelope (env) glycoprotein as an antigen which might provide protective immunity. Antisera prepared against purified gp 120 can neutralize HIV-1 in vitro. [Crowl, R., Cell 41: 979 (1985); Putney, S., Science 234: 1392 (1986); Ho, D., J. Virol. 61: 2024 (1987); Nara, P., Proc. Natl. Acad. Sci. USA 84: 3797 (1987)]. HIV-1 envelope antigen has been produced in different expression systems including Escherichia coli [Crowl, R., Cell 41: 979 (1985); Chang, T., Bio/Technology 3: 905 (1985); Dawson, G., J. Infect. Dis. 157: 149 (1988)] as well as mammalian [Chakrabarti, S., Nature 320: 535 (1986); Dewar, R., J. Virol. 63: 129 (1989); Rekosh, D., Proc. Natl. Acad. Sci. USA 85: 334 (1988); Whealy, M., J. Virol. 62: 4185 (1988)] yeast [Barr, P., Vaccine 5: 90 (1987)] and insect cells [Hu, S., Nature 328: 721 (1978); Rusche, J., Proc. Natl. Acad. Sci. USA 84: 6294 (1987)].

Live recombinant vaccinia virus expressing the entire HIV-1 env glycoprotein [Hu, S., J. Virol. 61: 3617 (1987)] or purified recombinant gp 120 env glycoprotein [Berman, P., Proc. Natl. Acad. Sci. USA 85: 5200 (1988)] were evaluated in chimpanzees as vaccine candidates. Active immunization with these vaccines induced a good cell-mediated immune response as well as cytotoxic T-cell activity to the env antigen [Zarling, J., J. Immunol. 139: 988 (1987)]. All experimental animals seroconverted as assayed by ELISA and Western blotting. However, immunized chimpanzees developed no or only low titers of neutralizing antibody to HIV-1. Challenge with live virus failed to protect chimpanzees against these vaccines. Type-specific HIV-1 neutralizing antibodies were found in chimpanzees early in infection against a variable domain (V3) within the C-terminus half of gp 120 [Goudsmit, J., Proc. Natl. Acad. Sci. USA 85: 4478 (1988)]. The recombinant gp 120 made in insect cells has also been shown to induce humoral immune response in goat (Rusche J., Proc. Natl. Acad. Sci. USA 84: 6294 (1987)]. Zagury [Nature 332: 728 (1988)] have demonstrated both anamnestic humoral and cellular immune reaction in humans using a vaccine virus recombinant expressing gp 160 [Chakrabarti, S., Nature 320: 535 (1986); Hahn, B., Proc. Natl. Acad. Sci. USA 82: 4813 (1985)]. Both group-specific cell-mediated immunity and cell-mediated cytotoxicity against infected T4 cells were also found. These results indicate that an immune state against HIV-1 can be obtained in humans using recombinant env-based vaccine. Recently, Desrosiers has shown that vaccination with inactivated whole simian immunodeficiency virus (SIV) can protect macaques against challenge with live SIV. [Proc. Natl. Acad. Sci. USA 86: 6353 (1989)]. These data provide hope that vaccine protection against human AIDS virus, HIV-1, infection may be possible.

Chanda discloses high level expression of the envelope glycoproteins of HIV-1 in the presence of rev gene using helper-independent adenovirus type 7 recombinants. [Virology 175: 535 (1990)]. Vernon discloses the ultrastructural characterization of HIV-1 gag subunit in a recombinant adenovirus vector system. [J. Gen. Virology 72: 1243 (1991)]. Vernon also discloses the preparation of the HIV-1 recombinant denoviruses Ad7-rev-gag and Ad4-rev-gag.

SUMMARY OF THE INVENTION

This invention provides a method of producing antibodies or cell mediated immunity to an infectious organism in a warm blooded mammal which comprises administering to said warm blooded mammal intranasally, intramuscularly, or subcutaneously, live recombinant adenoviruses in which the virion structural protein is unchanged from that in the native adenovirus from which the recombinant adenovirus is produced, and which contain the gene coding for the antigen corresponding to said antibodies or inducing said cell mediated immunity. The warm blooded mammal is preferably a primate, most preferably a human.

In its preferred embodiments, this invention provides a method of producing antibodies to human immunodeficiency virus (HIV-1), hepatitis B, hepatitis C, human papilloma virus, respiratory syncytial virus, rotavirus, or parainfluenza virus in a warm blooded mammal which comprises administering to said warm blooded mammal intranasally, intramuscularly, or subcutaneously, live recombinant adenoviruses in which the virion structural protein is unchanged from that in the native adenovirus from which the recombinant adenovirus is produced and which contain the gene coding for, respectively, human immunodeficiency virus, hepatitis B, hepatitis C, human papilloma virus, respiratory syncytial virus, rotavirus, or parainfluenza virus.

This invention also provides composition for producing antibodies or cell mediated immunity to an infectious organism in a warm blooded mammal, comprising live recombinant adenoviruses in which the virion structural protein is unchanged from that in the native adenovirus from which the recombinant adenovirus is produced, and which contain the gene coding for the antigen corresponding to said antibodies or inducing said cell mediated immunity, said composition being formulated in an intranasal, intramuscular, or subcutaneous dosage form.

Although this specification specifically refers to adenovirus of types 4, 5, or 7, live, infectious adenovirus of any type may be employed in this invention. Additionally, while the specification specifically refers to adenoviruses having an early region 3 (E3) deletion, adenoviruses which are attenuated, contain a temperature sensitive lesion, or a E1 deletion may also be used as a vector. Similarly, although specific reference has been made to vaccines producing antibodies to HIV, hepatitis B, hepatitis C, human papilloma virus, respiratory syncytial virus, rotavirus, or parainfluenza virus, our invention provides vaccines against any infectious agent containing an antigen to which a warm-blooded animal will produce antibodies or cell mediated immunity, and which antigen is coded for by a gene composed of up to about 3000 base pairs. Thus, for example, included within the scope of the invention are immunization against such diseases as influenza, hepatitis A, cholera, *E. coli*, pertussis, diphtheria, tetanus, shigellosis, gonorrhea, mycoplasma pneumonia, and the like.

In one embodiment, the method of treatment includes administering the recombinant adenovirus both prophylactically to an HIV-1 susceptible mammal and as immunotherapy following detection of HIV in said mammal. Regimens containing the following recombinant adenoviruses were used to produce the anti-HIV responses.

In a preferred embodiment, the method is a method of protecting a primate against HIV-1 infection comprising intranasal or intramuscular administration to said primate of an intranasal or intramuscular dosage of a recombinant adenovirus having a deletion in the E3 gene and an expression cassette containing a major late promoter, a tripartite leader sequence, part or all of the HIV-1 gp160 sequence and a polyadenylation signal sequence. Preferably the primate is a human. The expression cassette is inserted into the recombinant adenovirus between the E4 promoter and the inverted terminal repeat. Optionally the intranasal or intramuscular administration of recombinant adenovirus is followed by one or more intranasal or intramuscluar booster administrations of the recombinant adenovirus. The recombinant adenovirus is a serotype 4, 5 or 7 serotype adenovirus and optionally the expression cassette additionally comprises part of all of the coding sequence for the HIV-1 rev gene inserted in frame after the HIV-1 gp160 sequence and before the polyadenylation signal sequence. The HIV-1 gp160 sequence can be from the MN strain gp160 sequence or the LAV strain gp160 sequence. In an alternative embodiment, the HIV-1 gp160 sequence is replaced by a sequence encoding the gag-pro region of HV-1. In either embodiment, when the initial administration is followed by one or more intranasal or intramuscular booster administrations of the recombinant adenovirus, the last booster administration may be followed by an intramuscular injection of at least one booster immunization with an HIV-1 subunit antigen preparation, preferably containing an HIV-1 gag and/or env polypeptide sequence. For intranasal administration, the intranasal dosage administered is in the range of $1\times10^7$ pfu of virus and for intramuscular administration, the intramuscular dosage administered is in the range of $1\times10^7$ to $2\times10^9$ pfu of virus. The intranasal booster is administered in a dosage in the range of $1\times10^7$ to $1\times10^8$ pfu of virus and the intramuscular booster is administered in a dosage in the range of $1\times10^{10}$ to $8\times10^{10}$ pfu of virus. When a subunit antigen booster is employed, the subunit antigen preparation contains between 200 µg and 0.5 mg of HIV-1 polypeptide.

| Virus Name | Descriptive Name | ATCCName |
| --- | --- | --- |
| Ad7-env | Ad7-tplenv-tplHrev | VR-2299 |
| Ad7-gag | Ad7-tplgag-tplHrev | VR-2393 |
| Ad7-gag-1 | Ad7-rev-gag | VR-2392 |
| Ad4-env | Ad4-tplenv-tplHrev | VR-2293 |
| Ad4-gag | Ad4-tplgag-tplHrev | VR-2391 |
| Ad4-gag-1 | Ad4-rev-gag | VR-2390 |
| Ad5-env | Ad5-tplenv-tplHrev | VR-2297 |
| Ad5-gag | Ad5-tplgag-tplHrev | VR-2298 |
| Ad7-env$_{MN}$ | Ad7-tplenv$_{MN}$-tplHrev | VR- |
| Ad4-env$_{MN}$ | Ad4-tplenv$_{MN}$-tplHrev | VR- |
| Ad5-env$_{MN}$ | Ad5-tplenv$_{MN}$-tplHrev | VR- |

Referring to the above table Ad4, Ad5, and Ad7 refer to human adenoviruses types 4, 5, and 7 respectively in which the E3 region has been deleted. Env refers to the HIV envelope glycoprotein (gp 160) gene. Gag refers to the HIV gag/pro gene. Rev refers to the HIV regulatory gene. Hrev refers to an altered version of the rev gene where the nucleotide sequences were changed without changing the amino acid sequence employing codons that were frequently used in human genes. The sequence of Hrev is set forth in FIG. 2. Tpl refers to the upstream adenovirus tripartite leader sequence with an intervening sequence between the first and second leaders that are positioned in front of the recombinant genes. The constructs designated Ad7-env, Ad7-gag, Ad7-gag-1, Ad4-env, Ad4-gag, Ad4-gag-1, Ad5-env, and Ad5-gag contain either the gag or the env gene from the LAV strain of HIV and the constructs Ad7-env$_{MN}$, Ad4-env$_{MN}$, and Ad5-env$_{MN}$ contain the env gene from the MN strain of HIV. The recombinant adenoviruses made from the LAV and MN strains of HIV-1 are illustrative of recombinant adenoviruses covered by this invention. This invention also covers recombinant adenoviruses which include the env and/or gag genes from other strains of HIV-1.

Both the Ad-env and Ad-env$_{MN}$ adenoviruses were shown to replicate in human A549 cells and expressed recombinant env antigen in vitro demonstrating their capability of generating cell mediated, humoral, and secretory immunity in a mammal.

As described in detail below, intranasal administration of Ad-HIV recombinant viruses to naive chimpanzees resulted in both priming and boosting of both humoral and cell-mediated immune responses directed at HIV recombinant antigens. The recombinant adenoviruses administered to chimpanzees were shown to produce antibodies to the env and gag proteins of HIV. IgG antibodies specific for HIV were observed in nasal, saliva, and vaginal secretions following administration of the recombinant adenoviruses and IgA antibodies specific for HIV were observed in nasal and saliva secretions. The first set of recombinant viruses (Ad7) appeared to be shed the longest period of time and induce the best anti-Ad antibody response. The results also showed that administration of Ad-HIV vaccines by the intranasal route was superior to administration of enteric-coated recombinant viruses by the oral route.

Optimum immune responses directed at HIV antigens required primary infection one booster immunization with a heterotypic recombinant Ad-HIV to elicit strong anti-HIV binding antibodies. Intranasal administration of the Ad-HIV viruses effectively primed chimpanzees to respond with high titered neutralizing antibodies to HIV-1 following subsequent HIV-1 subunit protein booster immunization.

BRIEF DESCRIPTION OF THE DRAWINGS

FIG. 2 illustrates the DNA sequence of the expression cassette containing the HIV gp160 coding sequence and the Hrev coding sequence inserted into the E3 deleted region of Adenovirus serotype 7 as described in Example 6.

DETAILED DESCRIPTION OF THE INVENTION

Preparation of Representative Recombinant Adenoviruses

Figure 1:
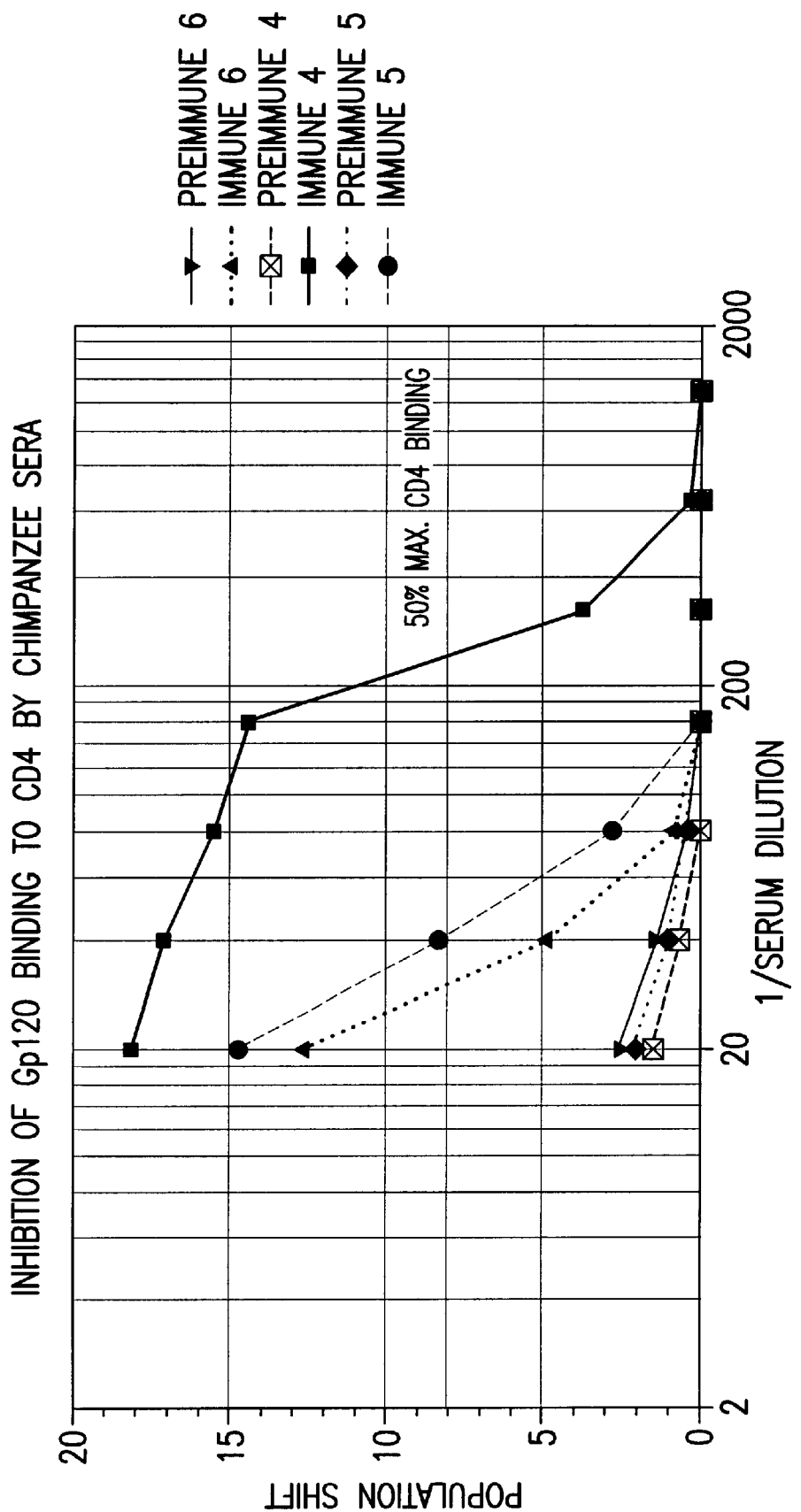
FIG. 1 shows the inhibition of gp120 binding to CD4 by sera induced in dogs by recombinant Ad-HIV vaccines.

The following Examples show the construction of representative recombinant adenoviruses of this invention. The recombinant viruses were propagated on A549 cells and subsequently titered on A549 cells.

EXAMPLE 1

Ad7-gag-1

The construction of recombinant adenoviruses containing the gene for the HIV envelope protein has been described [Chanda, P., Virology 175: 535 (1990)]; a similar procedure was used to incorporate gag and pro [see Vernon, S., J. Gen. Virology 72: 1243 (1991)]. Briefly, a DNA fragment containing the entire gag and pro coding regions (bp 335 to 2165) of HIV-1 strain LAV [Wain-Hobson, S., Cell 40: 9, (1985)] was constructed with a unique Sa/I site in front of the AUG codon of the gag gene and an XbaI site at bp 2165, for the insertion of the viral rev-responsive element (rre; bp 7178 to 7698). A 2.37 kb Sal fragment containing the three HIV-1 sequences was inserted at a SaI site in an expression cassette containing the adenovirus type 7 (Ad7) major late promoter (MLP), the tripartite leader (TPL) with an intervening sequence between the first and second leaders, and the hexon polyadenylation site (poly A) as described in Chanda [Virology 175: 535 (1990)]. The cassette was inserted 159 bp from the right end of an Ad7 genome [Sussenbach, The Adenoviruses, Ginsberg, ed., Plenum Press, pp. 34–124 (1984)] containing the HIV-1 rev gene [Feinberg, M., Cell 46: 807 (1986); Sodroski, J., Nature 321: 412 (1986)] in a deleted [79.5 to 88.4 map units (m.u.)] E3 region [Chanda, P., Virology 175: 535 (1990)].

EXAMPLE 2

Ad4-gag-1

Following the procedure for the construction of the Ad7-gag-1 recombinant adenovirus in Example 1, a similar expression cassette containing analogous Ad4 sequences and the three HIV coding regions were inserted at a site 139 bp from the right end of an Ad4 genome which contained HIV-1 rev in an E3 deletion between 76 and 86 m.u.

EXAMPLE 3

Ad5-env

Ad5-tplenv-tplHrev contains the entire coding sequence of HIV-1 (LAV strain) gp160 and a modified version of the rev gene, called Hrev. Both the env as well as rev gene are preceded by a synthetic copy of the Ad5 tripartite leader (Ad5-tpl). Ad5-tpl was chemically synthesized and was cloned in pTZ vector. Then the gp 160 DNA sequence was inserted behind the Ad5-tpl to create Ad5 -tplenv/PTZ18R clone. The Hrev (~360bp) was also chemically synthesized where the nucleotide sequences were changed without changing the amino acid sequence with the help of the codon usage. This was done to avoid homologous recombination as some identical sequences exist between env and rev. In an analogous way like Ad5-tplenv construct, Hrev gene was also inserted behind tpl in pTZ18R vector to create the plasmid, Ad5-tplHrev. The entire sequence containing Ad5-tplHrev was excised out and then inserted behind Ad5-tplenv to create the plasmid, Ad5-tplenv-tplHrev. This plasmid was then inserted in the deleted E3 region of Ad5 Marietta strain (78.8–85.7 mu deletion) at 78.8 mu. This plasmid was linearized with BglI enzyme and then mixed with 0–87 mu SnaB1 fragment that was derived from the wild-type purified Ad5 virus. After A549 cells were transfected with the DNA mixtures, recombinant virus plaques were picked, plaque purified three times, and their genomic structures were confirmed by restriction endonuclease site analysis of DNA extracted from infected cells by the method of Hirt. [J. Mol Bio. 26: 365 (1967)].

EXAMPLE 4

Ad5-gag

Ad5-tplgag-tplHrev contains the entire gag and pro region as well as the modified rev gene, Hrev. A copy of the Ad5 synthetic tripartite leader was placed in front of the gag and Hrev genes. A DNA fragment containing the entire gag and pro regions (bp 335 to 2165 of LAV strain of HIV-1) was constructed with a unique SalI site in front of AUG codon of the gag gene and an xba site at bp 2165, for the insertion of the viral rev-responsive element (rre; bp 7178–7698). Two separate plasmids Ad5-tplgag as well as Ad5-tplHrev were constructed in a similar way as described for Ad5-tplenv-tplHrev. Then the Ad5-tplHrev fragment was inserted behind Ad5-tplgag to create the plasmid Ad5-tplgag-tplHrev. Then the fragment Ad5-tplgag-tplHrev was inserted at the unique XbaI site at map position 78.8 of the Ad5 Marietta strain with an E3 deletion (78.8–85.7 mu E3 deletion). Then the final plasmid containing the Ad5 sequence was linearized and then mixed with the 0–87 mu SnaBl viral fragment for transfection. Recombinant plaques were picked up, plaque purified three times, and were checked by Hirt analysis of DNA extracted from the infected cells.

EXAMPLE 5

Enteric Coated Capsules

Recombinant adenoviruses were grown in A549 cells and harvested following 3 cycles of freeze-thawing. Clarified infected cell lysates were lypholized and 60 to 100 mg were packed into #2 gelatin capsules using a 1 ml syringe plunger under dehumidified conditions. The capsules were coated with a 10% cellulose acetate phthalate in acetone/100% Ethanol (1:1) by manually dipping each end 6 times with air drying between dips. A coating between 69 to 77 mg of cellulose acetate phthalate was formed under these conditions. Sample capsules were tested for resistance to simulated gastric fluid (0.32% pepsin, 0.2% NaCl pH 1.2) at 37

C using a VanKel Disintegration Testor apparatus for 1 hr. The capsules were inspected for holes or cracks and transferred to a 15 ml tube containing 10 ml of simulated intestinal fluid (1.0% pancreatin, 0.05 M monobasic potassium phosphate pH 7.5) and rotated at 37° C. All capsules tested were resistant to simulated gastric fluid for 1 hr at 37° C. with agitation and began to dissolve within 15 min. in simulated intestinal fluid. The amount of virus was titrated on confluent A549 cell monolayers by a plaque assay and the viral DNA stability confirmed by Hirt analysis.

EXAMPLE 6

Ad7-env$_{MN}$

The construction of recombinant adenoviruses containing the coding sequence of the env (gp 160) gene of MN strain of HIV-1 is described briefly as follows: The 125 bp (6243 to 6367) fragment of the amino ($NH_2$) terminus of the env (gp160) gene including the initiation codon (ATG) as well as consensus Kozak sequence was amplified by polymerase chain reaction (PCR) from the clone pMNST 1-8-9. This fragment was then cloned in pGEM vector and the resultant clone was designated as pGEMMNenv. The following fragments of DNA were isolated by digesting with the restriction enzymes KpnI and XbaI from the clone PAd5tpl$_{MN}$env 223 (6367 bp to 8816 bp), XhoI+KpnI fragment from PGEMenv and salI+XbaI fragment from pAd7tpl 18RD. All of these fragments were ligated together and the resultant clone was designated as pAd7tpl$_{MN}$env. This plasmid was then digested with XbaI and treated with calf intestine alkaline phosphatase (CIAP). The NheI+XbaI fragment of Hrev gene was then isolated from the plasmid, pAd7tplHrev 18RD. The clone that was obtained after ligating these two fragments together was designated as pAD7tpl$_{MN}$envtplHrev. This plasmid was then digested with NheI+ XbaI and then ligated to the E3 deletion plasmid of Ad7, pAd7ΔE3 (68 m.u. to 100 m.u. deletion) that was also digested with XbaI and then treated with CIAP. The resultant plasmid was designated as pAD7ΔE3tpl$_{MN}$envtpl$_{MN}$Hrev. This plasmid was digested with EcoRI and mixed with the EcoRI (0–87 m.u.) fragment of the Ad7 genomic DNA. A549 cells were then transfected with these DNAs. Recombinant plaques obtained from in vivo recombination were identified by the appropriate restriction digestion analyses of the Hirt DNA. The plaques were also identified by the production of gp160, gp120, and gp41 using appropriate antibodies on Western blots.

FIG. 2 illustrates the complete DNA sequence of the expression cassette containing the HIV gp160 coding sequence and the Hrev coding sequence inserted into the E3 deleted region of Adenovirus serotype 7 as described above. The first 200 bp tripartite leader sequence begins at bp 88, the HIV gp 160 sequence extends from bp 306 through bp 2879, the second tripartite leader sequence extends from bp 2886 through bp 3085 and the Hrev sequence extends from bp 3099 through 3449 in the Ad7 deleted E3 region.

EXAMPLE 7

Ad4-env$_{MN}$ and Ad5-env$_{MN}$

The construction of Ad4 and Ad5 recombinants are the same as that of Ad7-env$_{MN}$ except that for Ad4, EcoRI digested DNA from pAd4ΔE3tpl$_{MN}$envtplHrev was combined with the BclI (0–87 m.u.) fragment from the Ad4 genomic DNA to produce the recombinant Ad4 virus. Similarly for Ad5, MluI-digested DNA from pAd5ΔE3tpl$_{MN}$vtplHrev was combined with the SpeI (0–75 m.u.) fragment of Ad5 genomic DNA to produce the recombinant Ad5 adenovirus. Like Ad7, both Ad4 and Ad5 recombinants were obtained from A549 cells.

EXAMPLE 8

Subunit Antigen Preparation gp-120$_{MN}$ was prepared according to Kaufman, R. J., Nucleic Acid Res. 19: 4485 (1991) and was used in SAF-m adjuvant (Allison, A. C., J. Imm. Meth. 95: 157 (1986). gp-120$_{SF2}$ was prepared according to Scandella, C. J., AIDS Res. Human Retroviruses 9: 1233 (1993) and was used in MF-59 adjuvant (Keitel, W., Vaccine 11: 909 (1993)). HA-env$_{K17K}$ was prepared according to Kalayan, N., Vaccine 12: 753 (1994) and was used in SAF-m adjuvant.

Measurement of Replication and Antigen Expression

Human A549 cells were infected (MOI 10:1) with recombinant adenovirus types 4, 5, and 7 that contained either the LAV or MN env genes. At 34 hours post-infection, virus titer and env antigen expression was determined in duplicate samples. One dish of infected cells was subjected to 3 cycles of freeze thawing and the cell lysate was tested for the presence of infectious virus by plaque assay. The second culture dish was washed, detergent solubilized, and an aliquot of the cell lysate was loaded on to a 10% polyacrylamide gel. Following electrophoresis, the separated proteins were transferred to nitrocellulose by a Western blot apparatus. The transferred proteins were immunostained with anti-env reagents. A known standard, recombinant gp160, was added prior to electrophoresis. The resulting immunoblot was scanned by a densitometer and the amount of recombinant env determined. There were no significant differences seen between wild type adenoviruses and the recombinant adenoviruses expressing either the LAV or MN env gene. Both types of recombinant adenoviruses, LAV or MN, produced similar amounts of env antigen. Therefore, both types of Ad-env recombinants, LAV and MN, were able to grow in human A549 cells as well as their corresponding wild type adenovirus, and were able to express recombinant env antigen. These results therefore demonstrate that both the LAV and MN adenovirus recombinants are capable of generating cell mediated, humoral, and secretory immunity in a mammal. The data obtained are summarized in the table below.

ADENOVIRUS REPLICATION AND ANTIGEN EXPRESSION

| Adenovirus | pfu/cell × $10^2$ | µg env/$10^6$ cells |
| --- | --- | --- |
| Ad4 wild type | 5.4 | 0 |
| Ad4-env | 9.1 | 2.1 |
| Ad4-env$_{MN}$ | 6.8 | 2.7 |
| Ad5 wild type | 22 | 0 |
| Ad5-env | 86 | 5.4 |
| Ad5-env$_{MN}$ | 18 | 5.7 |
| Ad7 wild type | 18 | 0 |
| Ad7-env | 11 | 3.1 |
| Ad7-env$_{MN}$ | 7.8 | 3.6 |

Treatment Regimens

Immunogenicity of the recombinant adenoviruses for HIV was evaluated in chimpanzees under four treatment regimens (1, 2, 3, and 6), and in dogs two treatment regimens (4 and 5). Protection against HIV-1 infection was evaluated in chimpanzees in the sixth treatment regimen. The first regimen consisted of administering the recombinant adenovirus orally via an enterically coated capsule (Example 5) at 0, 7, and 26 weeks followed by an env+gag subunit protein booster using alum as an adjuvant. The second regimen consisted of further treating the chimpanzees that received regimen 1 at 46 and 58 weeks with additional boosters of recombinant adenovirus administered intranasally. The third treatment regimen consisted of administering recombinant adenovirus intranasally to naive chimpanzees at weeks 0, 24, and 52 followed by an env subunit booster at week 75. The fourth treatment regimen consisted of administering recombinant adenoviruses derived from both the LAV and MN strains of HIV-1 to dogs.

The fifth treatment regiment consisted of administering env subunit boosters to either previously immunized or control dogs. Each treatment group consisted of 6 previously immunized dogs and 2 control dogs. Of the previously immunized dogs, six had received Treatment Regimen 4 (Group A); six had received Treatment Regimen 4 (Group D); six had received Ad-env$_{HXB2}$ (expressing a portion of the HIV env V3 loop, derived from the LAV strain of HIV); and twelve had previously received Ad-env$_{HXB2}$ (expressing a portion of the HIV env V3 loop, derived from the MN strain of HIV) (prepared according to Robert-Guroff, M., J. Virol 68: 3459 (1994) and Veronese, F. D., J. Biol. Chem. 268: 25894 (1993)).

The sixth treatment regimen consisted of administering Ad-env$_{MN}$ recombinants to chimpanzees, followed by 0, 1 or 2 Ad-env$_{MN}$ booster immunizations using heterologous Ad vectors. The chimpanzees were then given one or two booster immunizations with env (gp$^{120}$$_{SF2}$) subunit antigen preparations, followed by a challenge with the SF2 strain of HIV.

The following table summarizes treatment regimens 1 and 2.

| TREATMENT REGIMENS 1 AND 2 | | | |
|---|---|---|---|
| Immunization | Time | Chimpanzees 1 and 2 | Chimpanzee 3 |
| Regimen 1 | | | |
| Primary* | 0 weeks | 1.5 × 10$^7$ pfu Ad7-env<br>2.0 × 10$^9$ pfu Ad7-gag-1 | 1.5 × 10$^7$ pfu Ad7-env |
| 1st Booster* | 7 weeks | 1.1 × 10$^{10}$ pfu Ad4-env<br>1.0 × 10$^{10}$ pfu Ad4-gag-1 | 1.1 × 10$^{10}$ pfu Ad4-env |
| 2nd Booster* | 26 weeks | 7.9 × 10$^{10}$ pfu Ad5-env | 7.9 × 10$^{10}$ pfu Ad5-env |
| 3rd Booster$^+$ | 34 weeks | 200 ug env in 0.2% alum<br>500 ug env in 0.2% alum | 200 µg env in 0.2% alum |
| Regimen 2 | | | |
| 1st Intranasal Boost | 46 weeks | 1.0 × 10$^8$ pfu Ad7-env<br>1.0 × 10$^8$ pfu Ad7-gag | 1.0 × 10$^8$ pfu Ad7-env |
| 2nd Intranasal Boost | 58 weeks | 1.0 × 10$^8$ pfu Ad4-env<br>1.0 × 10$^8$ pfu Ad4-gag | 1.0 × 10$^8$ pfu Ad4-env |

*Each dose was administered in enteric-coated gelatin capsules on 3 consecutive days.
$^+$Administered intramuscularly.

The following table summarizes treatment regimen 3.

| TREATMENT REGIMEN 3 | | | |
|---|---|---|---|
| Immunization | Time | Chimpanzees 4 and 5 | Chimpanzee 6 |
| Primary* | 0 weeks | 1.0 × 10$^7$ pfu Ad7-env<br>1.0 × 10$^7$ pfu Ad7-gag | 1.5 × 10$^7$ pfu Ad7-env |
| 1st Booster* | 24 weeks | 1.0 × 10$^7$ pfu Ad4-env<br>1.0 × 10$^7$ pfu Ad4-gag | 1.5 × 10$^7$ pfu Ad4-env |
| 2nd Booster* | 52 weeks | 1.0 × 10$^7$ pfu Ad5-env<br>1.0 × 10$^7$ pfu Ad5-gag | 1.5 × 10$^7$ pfu Ad5-env |
| 3rd Booster$^+$ | 75 weeks | 0.5 mg env | 0.5 mg env |

*Administered intranasally.
$^+$Administered intramuscularly.

The following Table summarizes treatment regimen 4.

| TREATMENT REGIMEN 4 | | | | | |
|---|---|---|---|---|---|
| Immunization | Time | Group A (n = 6) | Group B (n = 3) | Group C (n = 3) | Group D (n = 6) |
| Primary* | 0 weeks | Ad7-env$_{MN}$ | Ad7-env | Ad7-env$_{MN}$<br>$^+$Ad7-env | Ad5-env$_{MN}$ |
| 1st Booster* | 12 weeks | Ad5-env$_{MN}$ | Ad5-env | Ad5-env$_{MN}$<br>$^+$Ad5-env | Ad4-env$_{MN}$ |

*Each recombinant adenovirus was administered intratracheally at a dose of 1 × 10$^9$ per dog.

The following summarizes treatment regimen 5. Each group consisted of 6 dogs that were previously immunized, as described above, and 2 control dogs. Each group received 50 μg of the subunit in adjuvant at 0 weeks (20–28 weeks from the last Ad-env administration). Group A received gp120 SF2 in MF59 adjuvant; Group B received CHO-derived gp120$_{MN}$ (antibody purified) in SAF-m; Group C received Ad5-gp160$_{MN}$-derived gp160$_{MN}$ (lentil lectin purified) in SAF-m; Group D received Ad5-gp160$_{MN}$-derived gp160$_{MN}$ (lentil lectin purified) in MF59; and Group E received HA-env$_{K17K}$ (expressing a portion of the HIV env V3 loop). Twelve weeks later dogs were identically boosted with the same subunit, with the exception of Group D dogs which were reboosted with the HA-env$_{K17K}$.

The following table summarizes treatment regimen 6.

a 1 hr adsorption period the unbound material was washed away and the monolayers were overlaid with an 0.5% agar overlay medium. Plaques were allowed to develop for 7–10 days and plaques were visualized by neutral red staining, counted and the agar overlay was gently removed taking care not to disturb the cell monolayer. The cell sheet was transferred to nitrocellulose filter membranes (Millipore Type HA, 0.45 um), presoaked in 20× SSC and placed on the cell layer and left in contact with the cell monolayer for 2 to 4 minutes. The filters were peeled off, air-dried, and baked for 2 hr in a vacuum oven at 80° C. Nitrocellulose filters were washed twice in 3× SSc/0.1% SDS at room temperature and prehybridized and hybridized according to standard procedures [Poncet, D., J. Virol. Methods 26: 27 (1989)]. $^{32}$P-labeled oligoprobes were added to the hybridization

TREATMENT REGIMEN 6

| | Time | Chimpanzee Number | | | | |
|---|---|---|---|---|---|---|
| Immunization | (weeks) | 7 | 8 & 9 | 10 | 11 | 12 |
| Primary | 0 | Ad5-env$_{MN}$+ | Ad5-env$_{MN}$ | Ad5-env$_{MN}$, Ad7-env$_{MN}$, Ad4-env$_{MN}$ | AD5-env$_{MN}$ | Ad5 wild type |
| 1st Booster | 12 | — | Ad7-env$_{MN}$ | Ad5-env$_{MN}$, Ad7-env$_{MN}$, Ad4-env$_{MN}$ | Ad7-env$_{MN}$ | Ad7 wild type |
| 2nd Booster | 24 | — | — | — | Ad4-env$_{MN}$ | Ad4 wild type |
| Subunit Boost | 26 | gp120$_{SF2}$* | — | — | — | — |
| Subunit Boost | 38 | gp120$_{SF2}$ | gp120$_{SF2}$ | gp120$_{SF2}$ | — | — |
| Subunit Boost | 48 | — | — | — | gp120$_{SF2}$ | MF59 |
| Challenge | # | HIV$_{SF2}$ | HIV$_{SF2}$ | — | HIV$_{SF2}$ | HIV$_{SF2}$ |

+All Ad-env and Ad viruses were administered at a dose of 1.0 × 10$^7$ pfu/virus intranasally.
*50 μg HIV gp120$_{SF2}$ formulated in MF59 adjuvant was administered intramuscularly.
Chimpanzees 7, 8, and 9 were challenged at 40 weeks; 11 and 12 were challenged at 52 weeks, and 10 was not challenged.

Measurement of Immunogenicity: Treatment Regimen 1

Chimpanzee Inoculations

Three chimpanzees (2 males and 1 female) that were screened negative for the presence of neutralizing antibodies to human adenoviruses type 4, and 7 were evaluated using treatment regimen 1. Enteric-coated capsules containing recombinant adenoviruses were given using a stomach tube under anesthesia on three consecutive days. Two chimpanzees (1 and 2) received both env and gag recombinant viruses while the third chimp (3) received only env recombinant viruses.

Adenovirus-derived subunit preparations containing env or gag gene products were purified from infected A549 cell cultures [see Vernon, S., J. Gen. Virology 72: 1243 (1991) and Natuk, R., Proc. Natl. Acad. Sci. USA 89: 7777 (1992)]. Recombinant antigens were formulated with alum adjuvant and administered intramuscularly, 200 ug/dose env and 500 ug/dose gag particles.

Whole blood, serum, and stool samples were collected at different times during the course of the experiment. Whole blood was processed to obtain white blood cell populations for FACS, HIV CTL (using recombinant vaccinia viruses expressing HIV-env, HIV-gag, or the lac gene products), and for lymphoproliferative assays to purified HIV recombinant gp160, gp120, and p24. Serum and stool specimens were stored at −70° C. until use.

Detection of Recombinant Adenoviruses in Stool Specimens

Chimpanzee stool specimens were thawed and 10% (V/V) suspensions were made into antibiotic containing DMEM. Clarified stool suspensions were used to infect confluent A549 cell monolayers in 60 mm tissue culture dishes. After buffer (1×10$^6$ CPM) and incubated overnight at 42° C. DNA probes were prepared by which could detect either Ad4 fiber, Ad5 fiber, Ad7 fiber, HIV-env or HIV-gag specific sequences. [Wain-Hobson, Cell 40: 9 (1985)]. The filters were washed, autoradiographed, and hybridization signals were counted.

Adenovirus Neutralization Test Procedures

Serial 2-fold dilutions (starting with 1:4) of heat-inactivated (56 C fdor 30 min.) dog serum were made in 96-well microtiter plates (0.05 ml/well) and were mixed with 0.05 ml media containing 30–100 TCID$_{50}$ virus for 1 hr at 37° C. To each well 0.05 ml of media containing 2×10$^4$ A549 cells were added and the plates were incubated at 37° C. 5% CO$_2$ for 7–10 days. All samples were done in duplicate. Virus and uninfected cell controls were included in each assay for determining the end point in test sera. Titers were expressed as the reciprocal of the lowest dilution at which 50% cytopathic effect was observed.

Detection of Anti-HIV Antibodies by ELISA and Western Blotting

Detection of anti-HIV antibodies Chimpanzee antibody responses to HIV-1 antigens were measured by testing various dilutions by commercial ELISA and Western blot kits as instructed by the manufacturers (DuPont, Wilmington, Del.).

Results

Feces were collected from each chimpanzee prior to and after virus inoculation and stored at −70° C. Ten percent suspensions were prepared from each sample and were used to infect confluent A549 cell monolayers. After 7–10 days viral plaques were identified by neutral red staining and the cell monolayers were transferred to nitrocellulose membranes. Representative samples were hybridized with various labeled oligo-probes to detect sequences specific for Ad4, Ad5, Ad7, HIV-env, or HIV-gag genes. Identification of specific recombinant Ad-HIV viruses could be determined by this plaque hybridization technique. None of the recombinant viruses were shed into the feces for longer than 7 days p.i. Peak titers were always associated with 1–3 day samples and most likely represented the non-adsorbed virus inoculum. Previous chimp studies using Ad-HBsAg recombinants had indicated that Ad-HBsAg recombinants could be detected for 30–40 days p.i. With the enteric capsule route of administration, it appeared that these recombinant viruses did not replicate well in vivo.

Seroconversion to the serotype of the adenovirus vectors employed was determined by neutralization test procedures. Very low to modest anti-adenovirus serum titers were measured to all 3 serotypes used in each of the chimpanzees.

Seroconversion to recombinant HIV gene products were determined by either ELISA or Western blotting techniques. No ELISA response was detected in any of the chimpanzees prior to the second booster inoculation with the Ad5-env recombinant. Two weeks following Ad5-env inoculation anti-env responses could be measured in 2 of the 3 animals. Intramuscular injection of gag and/or env preparations had a slight boosting effect in 1 of the 3 animals. Western blot analysis appeared to be much more sensitive than the ELISA and had the further advantage of identification of which env and/or gag gene products were being recognized as being inmmunogenic. Low serum antibody titers were measured following both the primary Ad7 recombinant and first booster with Ad4 recombinants viruses. A significant increase in serum titer to env gene products was observed following the second booster immunization with the Ad5-env recombinant. Significant increases in the 2 animals which received gag gene products were seen following injection with subunit preparations. Despite relatively good Western blot titers to HIV antigens, only 1 of the 3 animals responded with serum neutralizing antibodies. This response in chimpanzee 2 was very low (titer of 10 to 20). These results are summarized in the following table.

RESULTS OBTAINED USING TREATMENT REGIMEN 1 gene products, the HIV-gag gene products, or the lac gene product (control for nonspecific cytotoxicity). A hint of HIV specific CTL-like activity was measured in this way.

Lymphoproliferative assays were performed to determine whether purified recombinant env (gp160, gp120) or gag (p24) preparations were capable of stimulating blastogenesis. No proliferation was measured after the primary inoculum and only 1 of the 3 animals show a lymphoproliferative response following administration of the first boost with Ad4 recombinant viruses. All 3 animals responded with proliferative responses after the second booster (Ad5-env) and the third boost (subunit preparations).

Measurement of Immunogenicity: Treatment Regimen 2

Chimpanzee Inoculations and Collection of Data

Three chimpanzees (2 males and 1 female) that were previously inoculated with Ad-HIV recombinant viruses in enteric-coated capsules and boosted with adenovirus-derived gag and/or env subunits (treatment regimen 1) were infected intranasally with Ad7-HIV viruses (week 46) and 12 weeks later (week 58) with Ad4-HIV viruses. Recombinant adenoviruses were given in tissue culture media diluted with phosphate saline buffer dropwise into the nostrils of chimpanzees under anesthesia. Two chimpanzees (numbers 1 and 2) received both env and gag recombinant viruses while the third chimp (number 3) received only env recombinant viruses.

Whole blood, serum, and stool samples were collected at different times during the course of the experiment, and processed as described in Regimen 1. Adenovirus detection in stool samples or nasal swabs, adenovirus neutralization test procedures, and detection of anti-HIV antibodies were performed according to the procedures described in Regimen 1.

Results

The first intranasal booster with Ad7 recombinants was given in one dose of $1 \times 10^8$ pfu's/chimpanzee. At the time of virus administration chimpanzees 3, 1, and 2 had serum anti-Ad7 neutralization titers of <4, 8, and 64 respectively from previous oral immunizations. Nasal swabs and stool samples were examined for the presence of shed recombinant viruses by a plaque hybridization technique. Recombinant Ad7-env was detected in nasal swabs up to 7 days p.i. in two of the animals. Recombinant Ad7-env and Ad7-gag

| Chimp Number | Recombinant Virus | Recombinant Virus Shedding Stools (Days) | Peak Anti-Adeno Neutralizing Titer | Western Blot Peak anti-HIV Titers env | Western Blot Peak anti-HIV Titers gag | Peak Anti-HIV Neutralizing Titer |
|---|---|---|---|---|---|---|
| 1 | Ad7-env, Ad7-gag-1 | 2, 2 | 128 | — | 20 | <10 |
|   | Ad4-env, Ad4-gag-1 | 2, 2 | 8 | — | 20 | <10 |
|   | Ad5-env | 7+ | 128 | 100 | — | <10 |
|   | subunit: env + gag |  |  | 100 | 1000 | <10 |
| 2 | Ad7-env, Ad7-gag-1 | 3, 2 | 64 | — | 20 | <10 |
|   | Ad4-env, Ad4-gag-1 | 1, 7 | 128 | 20 | 100 | <10 |
|   | Ad5-env | 7+ | 64 | 10000 | — | 20 |
|   | subunit: env + gag |  |  | 1000 | 10000 | 10 |
| 3 | Ad7-env | 2 | 6 | 20 | N/A* | <10 |
|   | Ad4-env | 1 | 128 | 20 | N/A | <10 |
|   | Ad5-env | 7+ | 512 | 1000 | N/A | <10 |
|   | subunit: env |  |  | 100 | N/A | <10 |

*N/A = not applicable.

Cell-mediated immunity was measured in peripheral blood mononuclear cell population obtained from chimpanzees. HIV specific CTL activity was measured by determining lysis of syngenic target cells that were infected with vaccinia virus recombinants that express either the HV-env were found to be present in stool samples from 5 to 12 days p.i. There was a correlation between the serum titer to Ad7 and the ability to detect recombinant viruses in nasal swabs and stool specimens. The two animals which displayed marginal anti-HIV antibody response were greatly augmented by the intranasal boost. The third animal was boosted to a lesser extent. Low titered neutralizing antibodies directed at HIV could now be detected in all three animals. Secretory antibodies were detected in nasal swab specimens which contained anti-gag and/or env binding antibodies. No signs or symptoms of respiratory disease were observed in these animals as a result of intranasal administration of the Ad7 recombinant viruses.

Three months later these chimpanzees were immunized with Ad4 recombinants at a single dose of $1 \times 10^8$ pfu's/chimpanzee/virus. These animals had serum anti-Ad4 neutralization titers between 128 to 256 from previous oral immunization at the time of intranasal challenge. At 3 days post-infection 2 of the animals (2 and 3) had a slight cough. The third animal (number 1) died on day 5 from a bacterial pneumonia (*Streptococcus pneumoniae* was isolated). The other two animals presented harsh sounds by auscultation and *S. pneumoniae* was isolated from both chimpanzees. Antibiotic treatments were initiated and both chimpanzees recovered.

H&E stained lung sections. There was a disagreement by experts as to whether these inclusions were caused by adenovirus or not. Several weeks later another chimpanzee experienced a similar fate at the same primate center and died. While it was likely that administration of recombinant adenoviruses had a only a minor role, if any, in causing the death of chimpanzee number I it was considered prudent to administer antibiotics prophylactically prior to and after any further intranasal administration of adenovirus recombinants to chimpanzees.

The following table shows the results obtained using treatment Regimen 1 and the Ad7-recombinants in Regimen 2.

RESULTS OBTAINED USING TREATMENT REGIMENS 1 AND 2

| Chimp Number | Recombinant Virus | Recombinant Virus Shedding Stools (Days) | Peak Anti-Adeno Neutralizing Titer | Western Blot Peak anti-HIV Titers | | Peak Anti-HIV Neutralizing Titer |
|---|---|---|---|---|---|---|
| | | | | env | gag | |
| 1 | Regimen 1 | | | | | |
| | Ad7-env, Ad7-gag-1 | 2, 2 | 128 | — | 20 | <10 |
| | Ad4-env, Ad4-gag-1 | 2, 2 | 8 | — | 20 | <10 |
| | Ad5-env | 7+ | 128 | 100 | — | <10 |
| | subunit: env + gag | | | 100 | 1000 | <10 |
| | Regimen 2 | | | | | |
| | Ad7-env, Ad7-gag | 12 | 512 | 10000 | 10000 | 10 |
| 2 | Regimen 1 | | | | | |
| | Ad7-env, Ad7-gag-1 | 3, 2 | 64 | — | 20 | <10 |
| | Ad4-env, Ad4-gag-1 | 1, 7 | 128 | 20 | 100 | <10 |
| | Ad5-env | 7+ | 64 | 10000 | — | 20 |
| | subunit: env + gag | | | 1000 | 10000 | 10 |
| | Regimen 2 | | | | | |
| | Ad7-env, Ad7-gag | 9 | 8192 | 1000 | 10000 | 20 |
| 3 | Regimen 1 | | | | | |
| | Ad7-env | 2 | 6 | 20 | N/A* | <10 |
| | Ad4-env | 1 | 128 | 20 | N/A | <10 |
| | Ad5-env | 7+ | 512 | 1000 | N/A | <10 |
| | subunit: env | | | 100 | N/A | <10 |
| | Regimen 2 | | | | | |
| | Ad7-env | 7 | 256 | 10000 | N/A | 10 |

*N/A = not applicable.

Upon retrospective examination of this situation several observations could be made. At the time of intranasal administration chimpanzee number 1 was already experiencing a fever and an abnormal Complete Blood Count. There was a disproportionate number of polymorphonuclear cells present and a 5% level of band cells (immature polymorphonuclear cells) taken together, this information indicated that there was a significant bacterial infection taking place prior to virus inoculation. Autopsy specimens taken from the lung, liver, spleen, and serum all tested negative for the presence of infectious adenovirus by tissue culture using 3 blind passages on susceptible A549 cell monolayers. Similar findings were obtained by plaque hybridization techniques. Lung and liver paraffin embedded samples tested negative for the presence of adenovirus antigens using a commercial immunofluorescent kit for adenovirus antigens. Inclusion bodies were observed in Measurement of Immunogenicity: Treatment Regimen 3
    Chimpanzee Inoculations and Collection of Data
    Three chimpanzees (2 males and 1 female) that were screened negative for the presence of neutralizing antibodies to human adenoviruses type 4, 5, and 7 were evaluated using treatment regimen 3. Two chimpanzees (numbers 4 and 5) received both env and gag recombinant viruses while the third chimp (number 6) received only env recombinant viruses. Antibiotics were administered prophylactically to the chimpanzees and no respiratory disorders were observed.

Whole blood, serum, and stool samples were collected at different times during the course of the experiment, and processed as described in Regimen 1. Adenovirus detection in stool samples or nasal swabs, adenovirus neutralization assays, and detection of anti-HIV antibodies were performed according to the procedures described in Regimen 1.

Detection of Inhibition of Gp120 Binding to CD4 Binding Sites

This assay is designed to measure the ability of chimpanzee anti-env antibodies to block the interaction of the HIV gp120 antigen with in natural ligand CD4. Various dilutions of chimpanzee sera were incubated with purified recombinant gp120 (1 ug/ml) 37° C. for 1 hour. HeLa CD4 positive cells ($5 \times 10^5$) were added to this mixture and incubated at 4° C. for 1 hour. The cells were washed 3 times with PBS-5%BSA and mixed with a FITC-labeled monoclonal antibody directed at the CD4 antigen (same site the gp120 binds to) and incubated at 4° C. for 1 hour. The cells were washed three times with the PBS-5% BSA and analyzed by flow cytometry.

Results

1st Immunization with Ad7-recombinants: Recombinant viruses were shed into feces for 22 to 34 days post-infection. No recombinant viruses were detected in nasal secretions taken at 2 weeks post-infection. Seroconversion to the serotype of the adenovirus vectors employed was determined by neutralization assays. Excellent anti-adenovirus serum titers were measured in all 3 chimpanzees to Ad7 serotypes used in each of the chimpanzees. Seroconversion to recombinant HIV gene products were determined by Western blotting. Four weeks following the primary immunization with Ad7-recombinants anti-env and anti-gag responses could be measured in 2 of the 3 chimpanzees. By 20 weeks post-infection all 3 animals had measurable antibodies to HIV antigens. Secretory antibodies were not found in nasal swabs taken within the first 4 weeks following primary immunization. All 3 chimpanzees failed to mount detectable anti-HIV neutralizing antibody responses.

1st Booster Immunization with Ad4-recombinants: Recombinant Ad4 viruses were shed into feces for 14–28 days post-infection. Examination of nasal swabs indicated that recombinant Ad4 viruses could be detected in all 3 chimpanzees for at least 7 days post-infection. Significant anti-Ad4 responses were mounted against the Ad4 serotype following intranasal administration. The magnitude was slightly lower then that measured against the Ad7-recombinant viruses. Excellent booster responses to gag and/or env antigens were measured in all three animals. Low titered (1:2) anti-gag and/or anti-env responses were measured in nasal swabs from Chimpanzees 4 and 5. Still no anti-HIV neutralizing antibodies were measured in any of the animals.

2nd Booster Immunization with Ad5-recombinants: Recombinant Ad5 viruses were shed into feces for 8 days post-infection. No recombinant viruses could be detected in nasal swabs at 0, 1, or 2 weeks post-inoculation. Anti-HIV IgG and IgA antibody response against env and gag could be measured in nasal swabs taken from 2 of 3 chimpanzees following Ad5-recombinant booster immunization by Western blot analysis. IgG and IgA anti-env and/or anti-gag antibodies were detected in saliva samples collected from 2 of 3 chimpanzees. Anti-env and -gag antibodies of the IgG class were detected in vaginal swabs taken from the single female chimpanzee.

Several samples which contained the greatest amount of anti-HIV antibodies of the IgA class were examined for the presence of secretory component. This was accomplished by substitution of polyclonal anti-secretory component (human) for polyclonal anti-IgA (human) in the HIV Western blot assay. Secretory anti-HIV IgA, containing secretory component, was detected in both nasal swabs and saliva samples in 1 of 3 chimpanzees.

3rd Booster Immunization with env Subunit: The strongest anti-env antibody responses were measured following subunit administration of these chimpanzees that had been primed with live recombinant adenoviruses. Anti-env antibody responses were detected in both serum and in various secretory samples collected from the nasal-oral cavity, vagina, and rectum. Peak antibody titers were detected at 4 weeks post administration with env subunit.

Serum anti-HIV neutralizing antibody titers of 320–640 were observed in all 3 chimpanzees. Antibodies directed against the gp120 V3 loop were detected by ELISA and against the gp120 CD4 binding site were detected by a FACS blocking assay. All three chimpanzees produced high ELISA titers (1000–9000) directed at the V3 loop (a region which contains the major neutralization determinant for HIV).

Chimpanzee sera collected at the height of the neutralizing response was evaluated for the presence of anti-CD4 binding site antibodies. All three animals had acquired antibodies that were capable of blocking the interaction between gp120 with CD4. The CD4 binding site is a conformational epitope and antibodies directed at this site are believed to be important in blocking uptake up cell-free HIV and perhaps capable of inhibiting gp120-CD4 syncytium induction. The results are shown in FIG. 1.

Nasal swab anti-env antibody titers of the IgG and IgA classes of immunoglobulins were boosted in 3 of 3 and 2 of 3 chimpanzees, respectively, following booster immunization with the env subunit. Similar results were observed in the saliva samples taken from these chimpanzees. Two of three chimpanzees had IgG anti-env antibodies present in rectal swabs and the single female chimpanzee had a strong IgG anti-env booster response measured in vaginal swabs. The presence of anti-HIV antibodies in mucosal secretions is critical because certain mucosal surfaces represent major sites for HIV infection.

Summary Tables: The following table shows the results obtained using treatment regimen 3.

RESULTS OBTAINED USING TREATMENT REGIMEN 3

| Chimp Number | Recombinant Virus | Recombinant Virus Shedding Stools (Days) | Peak Anti-Adeno Neutralizing Titer | Western Blot Peak anti-HIV Titers | | Peak Anti-HIV Neutralizing Titer |
|---|---|---|---|---|---|---|
| | | | | env | gag | |
| 4 | Ad7-env, Ad7-gag | 22, 22 | 1024 | 100 | 1000 | <10 |
| | Ad4-env, Ad4-gag | 14, 14 | 128 | 10000 | 10000 | <10 |
| | Ad5-env, Ad5-gag | 8, 8 | 32 | 10000 | 10000 | 20 |
| | subunit: env | N/A* | N/A | >10000 | 10000 | 640 |

-continued

RESULTS OBTAINED USING TREATMENT REGIMEN 3

| Chimp Number | Recombinant Virus | Recombinant Virus Shedding Stools (Days) | Peak Anti-Adeno Neutralizing Titer | Western Blot Peak anti-HIV Titers env | Western Blot Peak anti-HIV Titers gag | Peak Anti-HIV Neutralizing Titer |
|---|---|---|---|---|---|---|
| 5 | Ad7-env, Ad7-gag | 34, 27 | 1024 | 100 | 10000 | <10 |
|   | Ad4-env, Ad4-gag | 14, 14 | 512 | 10000 | 10000 | <10 |
|   | Ad5-env, Ad5-gag | 8, 8 | 32 | 10000 | 10000 | 20 |
|   | subunit: env | N/A | N/A | 1000 | 10000 | 320 |
| 6 | Ad7-env | 34 | 1024 | 100 | N/A | <10 |
|   | Ad4-env | 28 | 512 | 10000 | N/A | <10 |
|   | Ad5-env, gag | 8, 8 | 32 | 10000 | N/A | 40 |
|   | subunit: env | N/A | N/A | >10000 | N/A | 320 |

*N/A = not applicable.

The following table summarizes anti-HIV responses detected in chimpanzee secretions following intranasal booster immunization with the Ad5-HIV recombinants and after the intramuscular subunit boost (week 23 post boost).

Measurement of Immunogenicity: Treatment Regimen 4
Dog Inoculations and Collection of Data
Recombinant adenovirus was administered according to the table shown above for Treatment Regimen 4. Serum was

ANTI-HIV RESPONSES DETECTED IN SECRETIONS

| Chimp Number | Antigen Recognized | Weeks Post Boost** | Nasal IgA | Nasal IgG | Saliva IgA | Saliva IgG | Secretion Analyzed Vaginal IgA | Secretion Analyzed Vaginal IgG |
|---|---|---|---|---|---|---|---|---|
| 4 | env | 0 | —* | 360 | — | — | — | — |
|   |   | 1 | 180 | 360 | — | — | — | 90 |
|   |   | 2 | 180 | 2880 | 20 | 20 | — | 90 |
|   |   | 4 | 720 | 1440 | — | 20 | — | 360 |
|   |   | 23 | — | — | — | 80 | — | — |
|   |   | 24 | 90 | 720 | — | — | — | — |
|   |   | 25 | 90 | 2880 | 20 | 160 | — | 180 |
|   |   | 27 | 90 | 1440 | — | 160 | — | 720 |
|   | gag | 0 | — | 180 | — | — | — | — |
|   |   | 1 | 360 | 360 | — | 20 | — | 90 |
|   |   | 2 | 720 | 2880 | — | 20 | — | 90 |
|   |   | 4 | 720 | 720 | — | 20 | — | 90 |
|   |   | 23 | 90 | — | — | — | — | — |
|   |   | 24 | 90 | 90 | — | — | — | — |
|   |   | 25 | — | 90 | — | — | — | — |
|   |   | 27 | 90 | 360 | — | — | — | — |
| 5 | env | 0 | — | — | — | — | N/A+ | N/A |
|   |   | 1 | — | 90 | — | — | N/A | N/A |
|   |   | 2 | — | 2880 | — | — | N/A | N/A |
|   |   | 4 | — | 360 | — | — | N/A | N/A |
|   |   | 23 | — | — | — | — | N/A | N/A |
|   |   | 24 | — | 360 | — | 20 | N/A | N/A |
|   |   | 25 | 90 | 2880 | 20 | 80 | N/A | N/A |
|   |   | 27 | — | 720 | — | 320 | N/A | N/A |
|   | gag | 0 | — | — | — | — | N/A | N/A |
|   |   | 1 | — | 90 | — | — | N/A | N/A |
|   |   | 2 | 90 | 1440 | — | — | N/A | N/A |
|   |   | 4 | — | 360 | — | — | N/A | N/A |
|   |   | 23 | 90 | — | — | — | N/A | N/A |
|   |   | 24 | 90 | — | — | — | N/A | N/A |
|   |   | 25 | 90 | 90 | — | — | N/A | N/A |
|   |   | 27 | — | — | — | — | N/A | N/A |
| 6 | env | 0 | — | — | — | — | N/A | N/A |
|   |   | 1 | — | — | — | — | N/A | N/A |
|   |   | 2 | — | 1440 | 20 | 20 | N/A | N/A |
|   |   | 4 | — | 360 | — | — | N/A | N/A |
|   |   | 23 | — | — | — | — | N/A | N/A |
|   |   | 24 | — | 180 | — | — | N/A | N/A |
|   |   | 25 | — | 720 | — | 20 | N/A | N/A |
|   |   | 27 | — | 720 | — | — | N/A | N/A |

*equals less than 90 for nasal and vaginal swabs and less than 20 for saliva samples.
+N/A = not applicable.
**Post Ad5-boost. Subunit boost was administered 23 weeks after Ad5 boost.

collected at different times during the course of the experiment, and processed as described in Regimen 1. Adenovirus neutralization test procedures were performed according to the procedures described in Regimen 1. Detection of anti-HIV antibodies was performed according to the procedure described in Regimen 1 except that biotinolylated goat anti-dog $IgG_{(H+L)}$ was substituted for biotinylated goat anti-human $IgG_{(H+L)}$.

Serum samples were taken from immunized dogs at regular intervals after primary immunization and booster immunizations. Seroconversion to the serotype of the adenovirus vector employed was determined by neutralization test procedures. All of the dogs responded with strong anti-adenovirus titer to Ad7 vectors. Weaker anti-Ad5 responses were seen following Ad5 primary or booster inoculation. Seroconversion to env antigens was measured by Western blot and by HIV neutralization assays. Some dogs were able to produce low titer anti-env antibodies following primary immunization with recombinant Ad-env (LAV or MN). Significant booster responses to env antigen were observed in almost all of the dogs following heterotypic boosting with another recombinant Ad-env (LAV or MN) virus expressing the same type of env antigen.

Dogs that were primed with Ad7-env$_{MN}$ and boosted with Ad5-env$_{MN}$ had an average anti-HIV$_{MN}$ serum titer of >180 (range 45–>270) at 4 weeks post-boost. Dogs receiving the Ad5-env$_{MN}$ and Ad4-env$_{MN}$ combination had an average anti-HIV$_{MN}$ serum titer of >170 (range 45–>270) at this same time. There were no cross protective antibodies directed at the HIV$_{LAV}$ strain in any of these dogs. Dogs receiving the Ad7-env and Ad5-env combination had an average anti-HIV$_{LAV}$ serum titer of 55 (range 20–85) at 4 weeks post-boost and none of these dogs had anti-HIV$_{MN}$ titers. In at least one of the three dogs receiving the "recombinant cocktail" that contained both MN and LAV recombinant viruses had a anti-HIV$_{MN}$ serum titer of 90 and an anti-HIV$_{LAV}$ titer of 50. The other two dogs had anti-HIV$_{LAV}$ titers of 45 and 15.

These results demonstrate that the recombinant Ad-HIV$_{NM}$ viruses all elicit neutralizing antibodies directed at the MN strain of HIV. Low neutralizing titers were seen in 2 of 6 dogs in Groups 1 and 1 of 6 in Group 4 following the first immunization with Ad-env$_{MN}$ recombinants. Low to high neutralization titers were measured in all of the dogs in these two groups following booster immunization with heterotypic recombinant viruses. The neutralization titers produced were type specific and did not cross react with the LAV strain of HIV. When compared directly to other dogs treated with LAV recombinant Ad-env viruses, Ad-env$_{MN}$ recombinant viruses appeared to elicit higher type-specific neutralization titers in the dog standard pharmacological test procedure. Finally, the use of a "recombinant cocktail" which contains both MN and LAV recombinants appears to be capable of eliciting neutralizing antibodies to both strains of HIV.

Measurement of Immunogenicity: Treatment Regimen 5
HIV Subunit Administration in Dogs Thirty laboratory dogs that were either previously immunized twice with Ad-env recombinants (12–18 week intervals, with the 2nd immunization 20–28 weeks prior to the 1st subunit immunization) and ten (10) control dogs that have never been exposed to Ad-env recombinants were injected with one of five different HIV-env subunit preparations according to the description shown above for Treatment Regimen 5. All immunizations were administered by the subcutaneous route. Serum was collected at different times during the course of the experiment, and processed as described in Regimen 1. Adenovirus neutralization test procedures were performed according to the procedures described in Regimen 1.

Results

The results that were obtained are described below and provided in a summary table that follows.

1st Subunit Administration. All subunit vaccines administered to Ad-env "primed" dogs boosted anti-HIV$_{MN}$ neutralizing antibody responses. Two subunit preparations, A and C, were both examined for their ability to induce cross neutralizing responses to HIV$_{SF2}$. Heterologous boosting (i.e., Ad-env$_{MN}$ primed and gp-$^{120}$$_{SF2}$ boost) as well as homologous boosting (Ad-env$_{MN}$ primed and gp160$_{MN}$ boost) both stimulated anti-HIV$_{SF2}$ neutralizing antibody responses. Control dogs from groups B and C produced anti-env binding antibodies to HIV-env. Neutralizing antibody responses were not observed in control dogs following the first subunit administration.

2nd Subunit Administration. Administration of the second subunit did not appear to be as effective as a boosting agent compared to the first subunit administration. Group B dogs exhibited the greatest serum neutralizing antibody response (3–4 fold increase) of the five groups following the second booster immunization. Groups A and C showed two-fold increases following their second subunit administrations, while the HA-env antigen failed to significantly alter the geometric mean neutralizing titer of either Group D or E. Controls from all five groups produced anti-env binding antibodies. Functional neutralizing anti-HIV antibodies were observed only in the groups B, C, and D controls. Group A and E controls still failed to produce neutralizing antibody responses after the second subunit administration.

In summary, these results demonstrate that strong neutralizing antibody responses were elicited in all groups that were previously "primed" with Ad-HIV recombinants. After priming, high neutralizing antibody titers were observed in groups that were boosted heterologously (with gp120$_{SF2}$) and homologously (with gp120$_{MN}$). In the primed dogs, neutralizing antibodies were generated to both the MN and SF2 strains of HIV. Neutralizing antibody titers were still observed at twelve weeks, prior to the second boost. After the second boost, significant increases in neutralizing antibodies were observed in both gp120-boosted groups (Groups A and B).

Summary Table

The following table shows the results obtained using Treatment Regimen 5.

HIV SUBUNIT IMMUNIZATION IN Ad-HIV PRIMED DOGS

| Group[+] | n | First Subunit | Second Subunit | Peak Titer After 2nd Ad-HIV | Anti-HIV$_{MN}$ Responses* | | | |
|---|---|---|---|---|---|---|---|---|
| | | | | | 0 wk | 2 wk | 12 wk | 14 wk |
| A | 6 | gp120$_{SF2}$ | gp120$_{SF2}$ | 122 | 16 | 357 | 84 | 270 |
| | 2 | gp120$_{SF2}$ | gp120$_{SF2}$ | — | — | — | — | — |
| B | 6 | gp120$_{MN}$ | gp120$_{MN}$ | 141 | 17 | 883 | 229 | 472 |
| | 2 | gp120$_{MN}$ | gp120$_{MN}$ | — | — | — | — | 156 |
| C | 6 | gp160$_{MN}$ | gp160$_{MN}$ | 88 | 29 | 369 | 55 | 68 |
| | 2 | gp160$_{MN}$ | gp160$_{MN}$ | — | — | — | — | 100 |
| D | 6 | gp160$_{MN}$ | HA-env | 88 | 25 | 391 | 87 | 83 |
| | 2 | gp160$_{MN}$ | HA-env | — | — | — | — | 93 |
| E | 6 | HA-env | HA-env | 189 | 41 | 431 | 62 | 110 |
| | 2 | HA-env | HA-env | — | — | — | — | — |

[+]Each group consisted of 6 dogs that were previously immunized twice with Ad-Env$_{MN}$ and 2 control dogs that were not immunized.
*Reciprocal geometric mean neutralization titer to HIV$_{MN}$. Reciprocal genometric mean neutralization titers to of 98 and 42 to HIV$_{SF2}$ were observed for the previously immunized dogs of groups A and C respectively, at 2 weeks.

Measurement of Immunogenicity: Treatment Regimen 6
Chimpanzee Inoculations and Collection of Data Six female chimpanzees were selected on the basis of their serological profiles to human adenoviruses types 4, 5, and 7, and were treated according to the table shown above for Treatment Regimen 6. Their selection was based on a "best fit" for having the lowest possible serum neutralization titers directed at the various Ad-env vaccine combinations that were designated to be administered. Four chimpanzees that were either seronegative or weakly seropositive received either 1, 2, or 3 consecutive intranasal immunizations with recombinant Ad-env (12 week intervals) (Chimpanzees 7, 8, 9, and 1 1). One chimpanzee that was strongly seropositive (titers of 128 to all 3 Ad serotypes; Chimpanzee 10) was given a mixture of all 3 recombinants (each at a dose of 1×10$^7$ pfu) as a primary immunization and boosted 12 weeks later with the same mixture. All of the Ad-env immunized chimpanzees received an intramuscular immunization boost with 50 μg of gp120$_{SF2}$ HIV-env subunit formulated in MF59 adjuvant (MF59 adjuvant is described in Vaccine 11: 909 (1993)). One control chimpanzee (number 12) received 3 consecutive intranasal immunizations with wild-type human adenoviruses (12 week intervals) and an intramuscular immunization with the MF59 adjuvant alone at week 48. Antibiotics were administered prophylactically to all of the chimpanzees and no respiratory disorders were observed.

Whole blood, serum, and stool samples were collected at different times during the course of the experiment, and processed as described in Regimen 1. Adenovirus detection in stool samples, nasal or pharyngeal swab samples were done either by a plaque hybridization assay (described in Regimen 1) or by PCR technology (see below). Adenovirus neutralization assays and detection of anti-HIV antibodies were performed according to the procedures described in Regimen 1. Chinese hamster ovary cell (CHO)-derived gp120 or commercially purchased (American Biotechnologies, Cambridge, Mass.) HIV V3$_{MN}$ peptides were used as substitute antigen reagents in antibody binding assays.

PCR detection of recombinant Ad-env in chimpanzee stool samples was carried out with a commercially purchased PCR kit according to the supplier's instructions (Perkin Elmer Cetus, Norwalk Conn.). Briefly, about 250 μl of the stool samples was heated to 95° C. for 5 minutes and centrifuged in a microfuge at top speed for 2–3 minutes. The supernatant was saved. 1–10 μl per PCR reaction was used. Several tubes of master mix were prepared from the PCR kit and kept frozen at −20° C. For a 10 reaction tube, sterile water (615 μl), 10× buffer (100 μl), dATP (20 μl), dCTP (20 μl), dGTP (20_μl), and dT7P (20 μl) were mixed to make up the master mix. For each reaction, 79.5 μl of the master mix were used. On the day of the first PCR, a tube of master mix (10 rx) was thawed. To the master mix were added 10 μl of each of the oligomers, 5 μl of native Taq DNA polymerase, 50 μl water. The solution was mixed and about 90 μl was distributed to each reaction tube. The PCR was carried out in a 0.5 ml eppendorf tube. To each tube was added 10 μl of the stool supernatant. Thirty (30) cycles of PCR amplification were run at 95° C. for 1 hour, 45° C. for 1.5 hours, and 72° C. for 2 hours. A second PCR was performed with a 2.5 μl aliquot of the first PCR product as a DNA template and a corresponding oligo pair as primers. After 30 cycles of amplification, 10 μl of the reaction product was run on a 1.2% argose gel. A 800 bp DNA band was observed as a positive control for Ad7-env. The following primer pairs were used for nested PCR.

| Template Gene | 1st PCR | 2nd PCR | DNA Size |
|---|---|---|---|
| HIV-1 gp120$_{MN}$ | 5166/5209 | 5164/5208 | 800 bp |
| Ad4 fiber | 5467/5468 | 5469/5470 | 782 bp |
| Ad5 fiber | 5625/5523 | 5624/5522 | 423 bp |
| Ad7 fiber | 5505/5504 | 5503/5502 | 978 bp |

HIV specific CTL activity was measured by determining lysis of syngenic target cells that were infected with vaccinia virus recombinants that express either the HIV-env gene products, the HIV-gag gene products, or the lac gene product (control for nonspecific cytotoxicity).

Results

1st Immunization with Ad5-recombinants: Recombinant Ad5 virus was shed into fecal, pharyngeal, and/or nasal specimens for 0–7 days collected from chimpanzees that were seronegative or weakly seropositive to Ad5. Only the Ad5 recombinant was detected in the strongly seropositive chimpanzee immunized with the mixture of three recombinants. Wild-type adenovirus was shed for 56 days in the control chimpanzee that was weakly seropositive to Ad5.

Significant anti-Ad5 responses were produced in most of the chimpanzees, with the strongest response produced in the control animal immunized with the wild-type Ad5. Three of the four chimpanzees (numbers 7, 9 and 11) immunized with the single Ad5 recombinant produced weak anti-env antibody responses. Functional serum neutralizing anti-HIV antibodies were detected only in chimpanzee 5, which was originally seronegative to Ad5. Secretory anti-IgG anti-env antibodies were detected in vaginal, nasal, and saliva specimens collected from chimpanzee 11. Sporadic detection of env-specific CTL activity (specific lysis=10%) was observed in in vitro stimulated peripheral blood lymphocyte (PBL) populations obtained from chimpanzees 7, 8, 9, and 10 following the primary immunization with Ad5-env. Significant CTL responses were not observed in PBL obtained from chimpanzee 11.

2nd Immunization with Ad7-recombinants. Recombinant Ad7 viruses were shed into fecal, pharyngeal, and/or nasal specimens for 7–10 days in the three chimpanzees (numbers 8, 9, and 11) that were immunized with the Ad7-env alone and for 7 days in the chimpanzee (number 10) that was strongly seropositive to all 3 recombinant adenoviruses. Wild-type Ad7 was shed for 14 days in the control chimpanzee (number 12). Significant anti-Ad7 responses were developed in all Ad7 immunized animals with the best response observed in the control chimpanzee immunized with wild-type virus. Significant anti-env responses were boosted in 2 (numbers 9 and 11) of the 3 chimpanzees boosted with Ad7-env alone, while insignificant changes were observed in the animal given the mixed adenovirus preparation. Importantly, the two chimpanzees both contained functional neutralizing antibodies to $HIV_{MN}$. Chimpanzee 11 also had a very low cross-negative neutralizing antibody response directed at $HIV_{SF2}$. Nasal and saliva specimens collected from this chimpanzee also became positive for anti-env IgG antibodies. Vaginal anti-env IgG antibody responses were also boosted in chimpanzee 11. Still, anti-env antibody responses were not observed in any of the secretory fluids collected from the other chimpanzees. Again, only sporadic detection of env-specific CTL responses were detected in in vitro stimulated PBL populations prepared from chimpanzees 8, 9, and 10. As before, significant CTL responses were not observed in PBL populations obtained from chimpanzee 11.

3rd Immunization with Ad4-env recombinants. Recombinant Ad4-env was shed in stools for up to 3 days in the single animal (number 11) that was immunized with the Ad4-env alone. Ad4-env shedding was not detected in the strongly anti-Ad seropositive chimpanzee (number 10) after either immunization with the mixed Ad-env preparation. Wild-type Ad4 was shed for 7 days in chimpanzee 12. Both chimpanzees 11 and 12 made excellent anti-Ad4 antibody responses. The second booster immunization in chimpanzee 11 resulted with a significant boost in the anti-env antibody responses, including anti-$HIV_{MN}$ neutralizing antibody response. Nasal, vaginal, and saliva anti-env IgG antibody responses were boosted in samples collected from chimpanzee 11. Despite the generation of an excellent humoral anti-env immune response in chimpanzee 11, significant CTL responses were not observed.

1st Subunit boost. The heterologous $gp120_{SF2}$ subunit antigen preparation was administered to chimpanzee 7, 26 weeks after the primary Ad5-env immunization. The subunit immunization was very successful in boosting the anti-env antibody response. A high titered neutralizing anti-$HIV_{MN}$ response (>400)was observed along with a lower anti-$HIV_{SF2}$ response (100). The subunit administration also elicited strong anti-env IgG antibody responses in nasal and vaginal secretions, as well as weaker anti-env responses in rectal secretions. One (chimpanzee 9) of the two animals given the (Ad5-env)/(Ad7-env) combination also showed excellent anti-env booster antibody responses following subunit administration. This animal had similar anti-$HIV_{MN}$ and anti-$HIV_{SF2}$ neutralizing titers as seen in chimpanzee 1. Weak anti-env IgG responses were observed in nasal, rectal, saliva, and vaginal secretions collected from this animal. The other chimpanzee (number 8) had a much weaker, but still significant anti-env response induced following subunit administration, but this response did not include functional neutralizing antibodies to HIV. Nor were anti-env antibodies detected in any of the secretions collected from this chimpanzee. Chimpanzee 11 which received the (Ad5-env)/(Ad7-env)/(Ad4-env) combination also showed an excellent anti-env antibody booster response. This included a very high neutralization titer (>1400) to $HIV_{MN}$ and high (>400) titers to $HIV_{SF2}$. Excellent anti-env IgG antibody responses were observed in vaginal, nasal, and saliva specimens. A weak anti-env response was observed in pharyngeal secretions. The subunit did not have a significant effect on the anti-env antibody response (serum or secretory) of chimpanzee 10 (the strongly anti-Ad seropositive animal), Sporadic anti-env CTL activity was detected in in vitro stimulated PBL populations collected only from chimpanzees 7 and 8 following subunit administration. Similar analysis of in vitro stimulated lymph node cells (obtained from a lymph node biopsy located in close proximity to the subunit inoculation site) revealed that cells obtained only from chimpanzee 8 (basically a non-humoral responder) contained significant CTL activity directed at both $env_{SF2}$ and $env_{MN}$.

2nd Subunit boost. Only chimpanzee 7 received a second subunit immunization. This second immunization resulted with a significant boost in the anti-env antibody response, including high titered anti-$HIV_{MN}$ (>200) and low (<100) anti-$HIV_{SF2}$ neutralizing antibody responses. Excellent anti-env IgG responses were observed in vaginal, nasal, and rectal specimens. Sporadic anti-HIV CTL activity was also seen in PBL populations.

$HIV_{SF2}$ Challenge of Immunized and Control Chimpanzees. A cell-free $HIV_{SF2}$ challenge was administered intravenously to five of the six chimpanzees (7, 8, 9, 11, 12). The challenge stock dilution of 1/40 was shown to productively infect control chimpanzees within 3 to 4 weeks. The chimpanzees were monitored for signs of HIV infection for a period of 10 weeks. HIV could be co-cultured from PBLs obtained from control chimpanzee 12 collected at 4 and 6 weeks post-challenge. Anti-gag antibody responses were readily measurable (another indication of HIV infection since the recombinant vaccines lacked gag determinants) in serum samples collected at 6, 8, and 10 weeks post-challenge. All other chimpanzees were protected from the HIV challenge at 10 weeks.

These results demonstrate that the intranasal administration of the Ad-env recombinants (particularly Ad7-$env_{MN}$, Ad5-$env_{MN}$, Ad4-$env_{MN}$ or a combination thereof) elicited the production of neutralizing antibodies against HIV-1. Neutralizing antibodies were produced following the first administration of the Ad-env recombinants, and the titer was increased through the use of one or more booster intranasal immunizations with the Ad-env recombinants. Antibody response to both the MN and SF2 strains of HIV was farther boosted through the administration of one or more inoculations with an env (gp120) subunit antigen preparation (particularly $gp120_{SF2}$). Most importantly, protection against HIV-1 infection was demonstrated following the administration of the Ad-env/subunit booster treatment regimen.

What is claimed is:

1. A method of producing an immune response against HIV-1 infection in a human comprising intranasal administration to said human an intranasal dosage of a recombinant adenovirus having a deletion in the E3 gene and an expression cassette containing a major late promoter, a tripartite leader sequence, part or all of the HIV-1 gp160 sequence and a polyadenylation signal sequence, said cassette being inserted into said recombinant adenovirus between the E4 promoter and the inverted terminal repeat of said recombinant adenovirus, wherein said intranasal administration of the recombinant adenovirus is followed by one or more intranasal or intramuscular booster administrations of said recombinant adenovirus.

2. The method of claim 1 wherein said adenovirus is a serotype 4, 5 or 7 serotype adenovirus.

3. The method of claim 2 wherein said expression cassette additionally comprises part or all of the coding sequence for the HIV-1 rev gene inserted in frame after the HIV-1 gp160 sequence and before the polyadenylation signal sequence.

4. The method of claim 3, wherein said HIV-1 gp160 sequence is the MN strain gp160 sequence or the LAV strain gp160 sequence.

5. The method of claim 3 wherein said HIV-1 gp160 sequence is replaced by a sequence encoding the gag-pro region of HIV-1.

6. The method of claim 1 wherein said one or more intranasal or intramuscular booster administrations of said adenovirus are followed by an intramuscular injection of at least one booster immunization with an HIV-1 subunit antigen preparation, wherein said subunit antigen preparation contains an HIV-1 gag and/or env polypeptide sequence.

7. The method of claim 1 wherein said intranasal dosage administered is in the range of $1 \times 10^7$ pfu of virus.

8. The method of claim 1 wherein said intranasal booster is administered in a dosage in the range of $1 \times 10^7$ to $1 \times 10^8$ pfu of virus.

9. The method of claim 1 wherein said intramuscular booster is administered in a dosage in the range of $1 \times 10^{10}$ to $8 \times 10^{10}$ pfu of virus.

10. The method of claim 6 wherein said subunit antigen preparation contains between 200 µg and 0.5 mg of HIV-1 polypeptide.

11. A method of producing an immune response against HIV-1 infection in a human comprising the steps of (i) intranasal administration to said human an intranasal dosage of a recombinant adenovirus serotype 4, 5 or 7 having a deletion in the E3 gene and an expression cassette containing a major late promoter, a tripartite leader sequence, part or all of the HIV-1 gp160 sequence, part or all of the coding sequence for the HIV-1 rev gene inserted in fie after the HIV-1 gp160 sequence and a polyadenylation signal sequence, said cassette being inserted into said recombinant adenovirus between the E4 promoter and the inverted terminal repeat of said recombinant adenovirus; and (ii), followed by one or more intranasal or intramuscular booster administrations of said recombinant adenovirus.

12. The method of claim 11 wherein said HIV-1 gp160 sequence is replaced by a sequence encoding the gag-pro region of HIV-1.

13. A method of producing an immune response against HIV-1 infection in a human comprising intramuscular administration to said human an intramuscular dosage of a recombinant adenovirus having a deletion in the E3 gene and an expression cassette containing a major late promoter, a tripartite leader sequence, part or all of the HIV-1 gp160 sequence and a polyadenylation signal sequence, said cassette being inserted into said recombinant adenovirus between the E4 promoter and the inverted terminal repeat of said recombinant adenovirus, wherein said intramuscular administration of the recombinant adenovirus is followed by one or more intranasal or intramuscular booster administrations of said recombinant adenovirus.

14. The method of claim 13 wherein said adenovirus is a serotype 4, 5 or 7 serotype adenovirus.

15. The method of claim 13 wherein said expression cassette additionally comprises part or all of the coding sequence for the HIV-1 rev gene inserted in frame after the HIV-1 gp160 sequence and before the polyadenylation signal sequence.

16. The method of claim 15 wherein said HIV-1 gp160 sequence is the MN strain gp160 sequence or the LAV strain gp160 sequence.

17. The method of claim 15, wherein said HIV-1 gp160 sequence is replaced by a sequence encoding the gag-pro region of HIV-1.

18. The method of claim 13 wherein said one or more intranasal or intramuscular booster administrations of said adenovirus are followed by an intramuscular injection of at least one booster immunization with an HIV-1 subunit antigen preparation, wherein said HIV-1 subunit antigen preparation contains an HIV-1 gag and/or env polypeptide sequence.

19. The method of claim 13 wherein said intramuscular dosage administered is in the range of $1 \times 10^7$ to $2 \times 10^9$ pfu of virus.

20. The method of claim 13 wherein said intranasal booster is administered in a dosage in the range of $1 \times 10^7$ to $1 \times 10^8$ pfU of virus.

21. The method of claim 13 wherein said intramuscular booster is administered in a dosage in the range of $1 \times 10^{10}$ to $8 \times 10^{10}$ pfu of virus.

22. The method of claim 18 wherein said subunit antigen preparation contains between 200 µg and 0.5 mg of HIV-1 polypeptide.

23. A method of producing an immune response against HIV-1 infection in a human comprising the steps of (i) intramuscular administration to said human an intramuscular dosage of a recombinant adenovirus serotype 4, 5 or 7 having a deletion in the E3 gene and an expression cassette containing a major late promoter, a tripartite leader sequence, part or all of the HIV-1 gp160 sequence, part or all of the coding sequence for the HIV-1 rev gene inserted in frame after the HIV-1 gp160 sequence and a polyadenylation signal sequence, said cassette being inserted into said recombinant adenovirus between the E4 promoter and the inverted terminal repeat of said recombinant adenovirus; and (ii), followed by one or more intranasal or intramuscular booster administrations of said recombinant adenovirus.

24. The method of claim 23 wherein said HIV-1 gp160 sequence is replaced by a sequence encoding the gag-pro region of HIV-1.

* * * * *

UNITED STATES PATENT AND TRADEMARK OFFICE
CERTIFICATE OF CORRECTION

PATENT NO.    : 6,511,845 B1  
DATED         : January 28, 2003  
INVENTOR(S)   : Alan R. Davis et al.

It is certified that error appears in the above-identified patent and that said Letters Patent is hereby corrected as shown below:

<u>Title page,</u>
Insert -- [73] Assignee: American Home Products Corporation, Madison NJ (US) --

Signed and Sealed this

Twenty-ninth Day of April, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,511,845 B1                                              Page 1 of 1
DATED         : January 28, 2003
INVENTOR(S)   : Alan R. Davis It is certified that error appears in the above-identified patent and that said Letters Patent is hereby corrected as shown below:

Column 4,
Line 32, after "Ad7-tplenv$_{MN}$-tplHrev       VR-" insert -- 2462 --
Line 33, after "Ad4-tplenv$_{MN}$-tp1Hrev       VR-" insert -- 2463 --
Line 34, after "Ad5-tplenv$_{MN}$-tp1Hrev       VR-" insert -- 2464 --

Signed and Sealed this

Fifth Day of August, 2003

JAMES E. ROGAN
*Director of the United States Patent and Trademark Office*